(12) United States Patent
Petersen et al.

(10) Patent No.: US 6,616,606 B1
(45) Date of Patent: Sep. 9, 2003

(54) PATIENT MONITORING SYSTEM

(75) Inventors: Eric G. Petersen, Aloha, OR (US); Herbert S. Weiner, Portland, OR (US)

(73) Assignee: Welch Allyn Protocol, Inc., Skaneateles Falls, NY (US)

( * ) Notice: Subject to any disclaimer, the term of this patent is extended or adjusted under 35 U.S.C. 154(b) by 0 days.

(21) Appl. No.: 09/861,095

(22) Filed: May 18, 2001

Related U.S. Application Data

(60) Provisional application No. 60/205,412, filed on May 19, 2000.

(51) Int. Cl.$^7$ ................................................ A61B 5/00
(52) U.S. Cl. ...................................... 600/300; 128/903
(58) Field of Search ................................. 600/300, 301; 128/903, 904; 340/2.1, 825; 370/216–228, 254–258; 714/2–4, 8; 455/7, 8, 9

(56) References Cited

U.S. PATENT DOCUMENTS 5,626,630 A * 5/1997 Markowitz et al. ......... 128/903
5,915,208 A * 6/1999 Collyer ........................ 455/8
6,440,067 B1 * 8/2002 DeLuca et al. .............. 600/300

* cited by examiner

Primary Examiner—Eric F. Winakur
Assistant Examiner—David J. McCrosky
(74) Attorney, Agent, or Firm—Wall Marjama & Bilinski

(57) ABSTRACT

A wireless medical telemetry system includes at least one wireless patient monitor configured to monitor a patient by collecting vital signs data from the patient, and a first central station associated with one or more wireless transceivers, and adapted to establish communications with the at least one patient monitor and receive the vital signs data via the one or more wireless transceivers. A second central station is associated with the one or more wireless transceivers, and adapted to receive vital signs data via the one or more wireless transceivers. The second central station is configured to automatically attempt to establish communications with the at least one patient monitor and receive the vital signs data in place of the first central station in the event the communications between the first central station and the at least one patient monitor are lost. There is also a method for monitoring a patient.

10 Claims, 17 Drawing Sheets

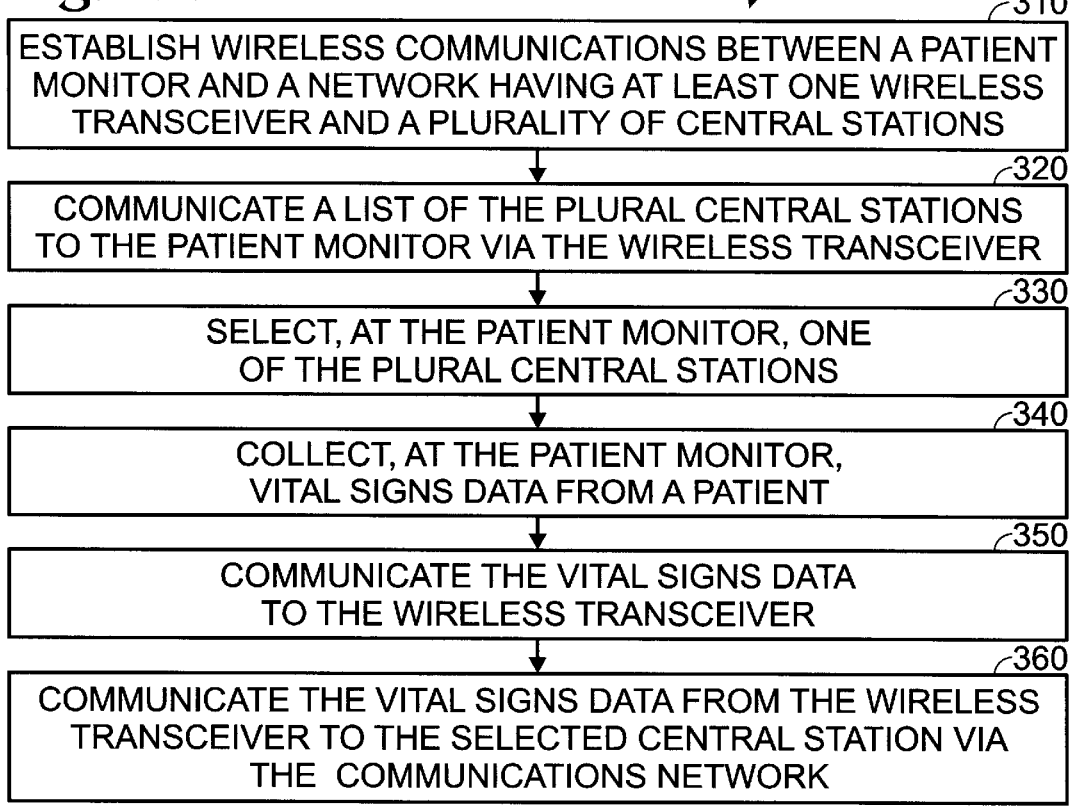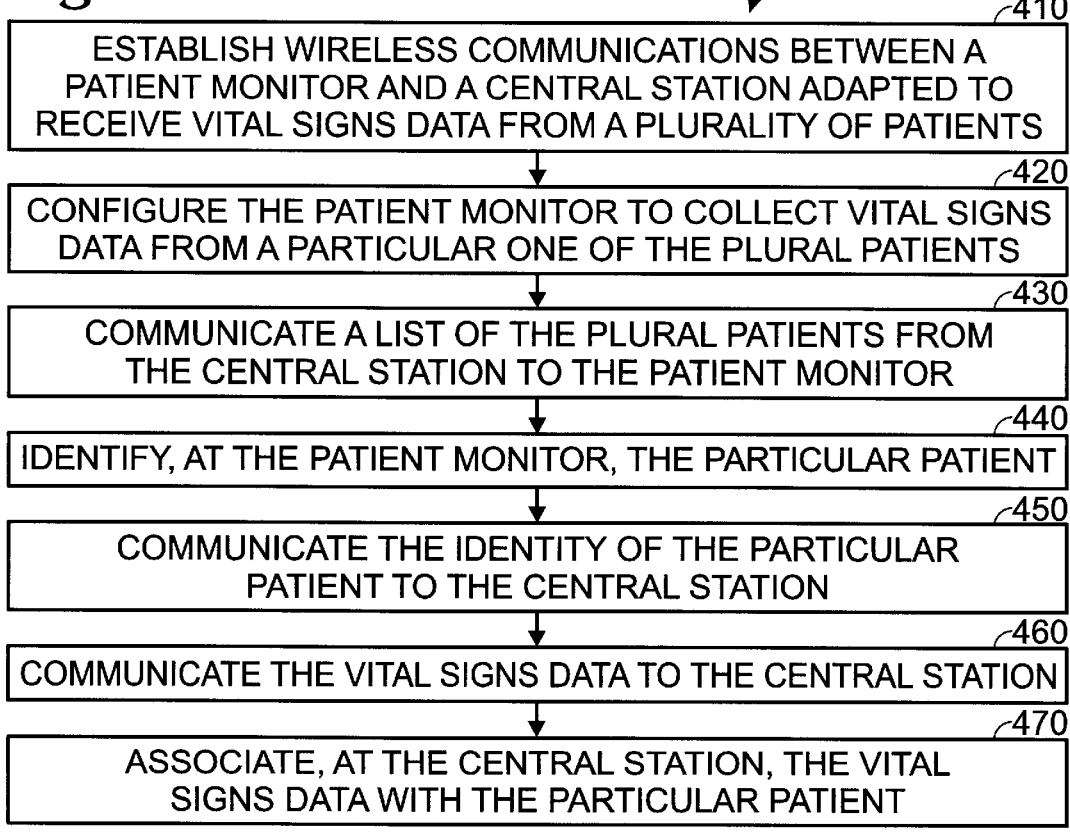

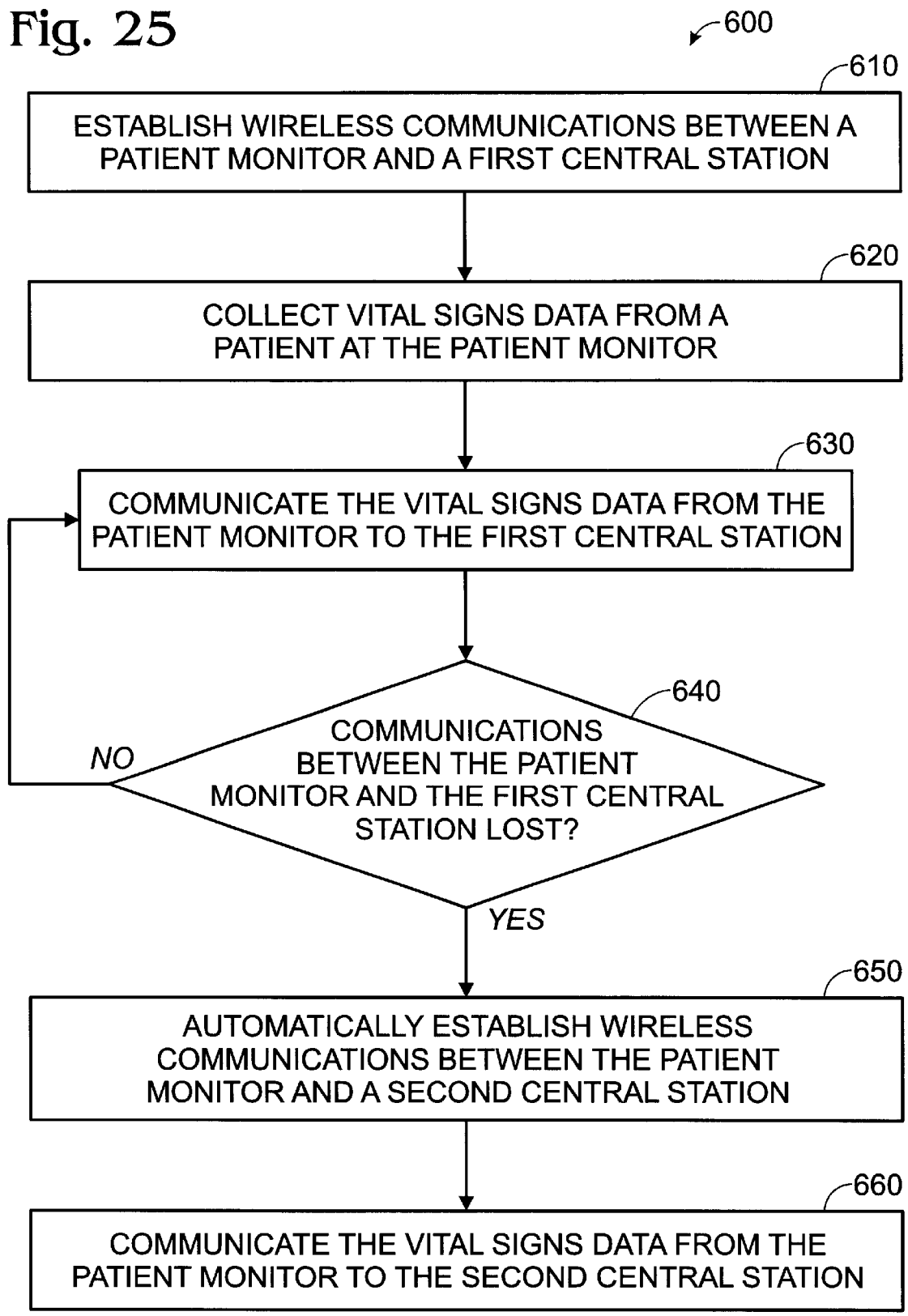

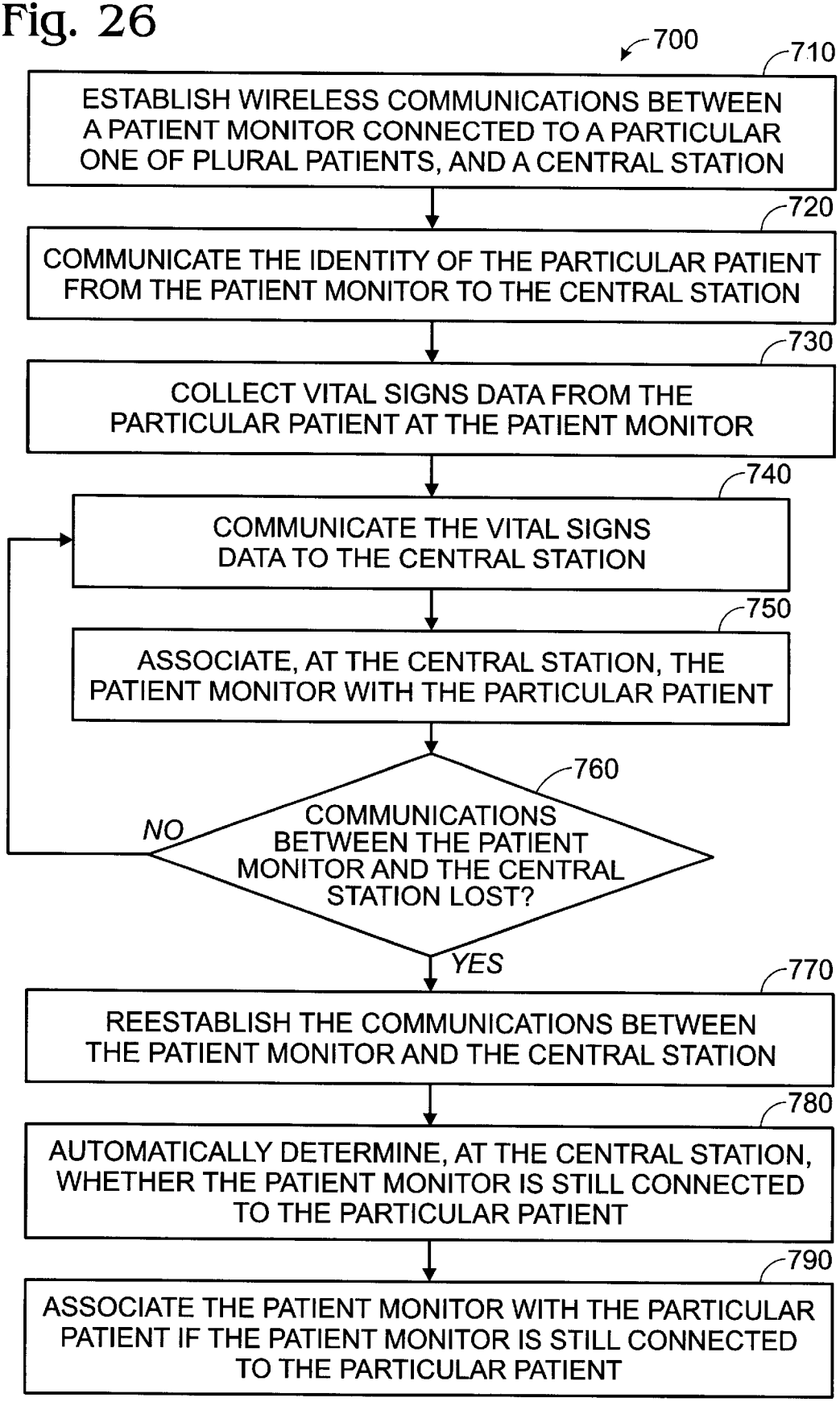

PATIENT MONITORING SYSTEM

CROSS-REFERENCE TO RELATED APPLICATIONS

This application claims priority to U.S. Provisional Patent Application Serial No. 60/205,412, filed May 19, 2000 and entitled PATIENT MONITORING SYSTEM. The subject matter of this application is incorporated herein by this reference.

FIELD OF THE INVENTION

The present invention relates generally to monitoring the vital signs of one or more patients, and more particularly to a system and method for monitoring patients via wireless communications.

BACKGROUND

Devices for measuring various physiological parameters, or "vital signs," of a patient such as temperature, blood pressure, heart rate, heart activity, etc., have been a standard part of medical care for many years. Indeed, the vital signs of some patients (e.g., those undergoing relatively moderate to high levels of care) typically are measured on a substantially continuous basis to enable physicians, nurses and other health care providers to detect sudden changes in a patient's condition and evaluate a patient's condition over an extended period of time. However, since most hospitals and other medical facilities care for numerous patients assigned to numerous different rooms, it can be difficult for a finite number of clinicians to monitor multiple patients on a continuous basis. In an effort to alleviate this problem, some medical monitoring systems have been developed to enable the vital signs data collected from patients to be conveyed to a central location, thereby allowing one or a few clinicians to simultaneously monitor multiple patients in different locations. However, many of such prior systems have not allowed the monitored patients to move about the hospital. Although a few "mobile" monitoring systems have been attempted, such systems are difficult to use and prone to failure resulting in the loss of a patient's vital signs data.

SUMMARY

A wireless medical telemetry system includes at least one wireless patient monitor configured to monitor a patient by collecting vital signs data from the patient, and a first central station associated with one or more wireless transceivers, and adapted to establish communications with the at least one patient monitor and receive the vital signs data via the one or more wireless transceivers. The invention also includes a second central station associated with the one or more wireless transceivers, and adapted to receive vital signs data via the one or more wireless transceivers. The second central station is configured to automatically attempt to establish communications with the at least one patient monitor and receive the vital signs data in place of the first central station in the event the communications between the first central station and the at least one patient monitor are lost.

The invention may also be characterized as a method for monitoring a patient that includes the steps of (i) establishing wireless communications between a patient monitor and a first central station, (ii) collecting vital signs data from a patient at the patient monitor, (iii) communicating the vital signs data from the patient monitor to the first central station, and, if communications between the patient monitor and the first central station are lost, (iv) automatically establishing wireless communications between the patient monitor and a second central station, and communicating the vital signs data from the patient monitor to the second central station.

Other characterizations of the invention and the advantages of the present invention will be understood more readily after a consideration of the drawings and the Detailed Description.

BRIEF DESCRIPTION OF THE DRAWINGS

FIG. 22 is a flowchart diagram of an exemplary method for monitoring a patient at a central location in accordance with the present invention.

FIG. 23 is a flowchart diagram of another exemplary method for monitoring a patient at a central location in accordance with the present invention.

FIG. 25 is a flowchart diagram of another exemplary method for monitoring a patient at a central location in accordance with the present invention.

FIG. 26 is a flowchart diagram of another exemplary method for monitoring a patient at a central location in accordance with the present invention.

DETAILED DESCRIPTION

From an overview, and as will be described in detail below, a system and method for monitoring patients is described that affords communication between plural patient monitors and plural central monitoring stations. The system and method is designed to allow the patient monitors to communicate with the central monitoring stations by using any known communication connection (such as to-be-described access points) located anywhere using any known communications technology (such as the IEEE 802.11 standard for wireless communication) that provides a communication channel. The to-be-described system and method also makes it possible for a clinician to view patient data on a display component of the patient monitor via any known communication channel such as the Internet. For example, the clinician could view patient data using known web browsers.

The to-be described system and method also includes a so-called "rendezvous process" of establishing communications with one or more central stations. As will be shown in connection with the description of FIG. 11, the rendezvous process may be carried out in any of a variety of different ways, and may vary depending on whether wireless or wired communications are used, as well as on whether the patient monitor is establishing a new communications connection or reestablishing prior communications which were lost or terminated.

The patient monitors of the to-be-described system are also constructed to function both as part of a network of patient monitors and central stations, as well as stand-alone patient monitors.

Figure 1:
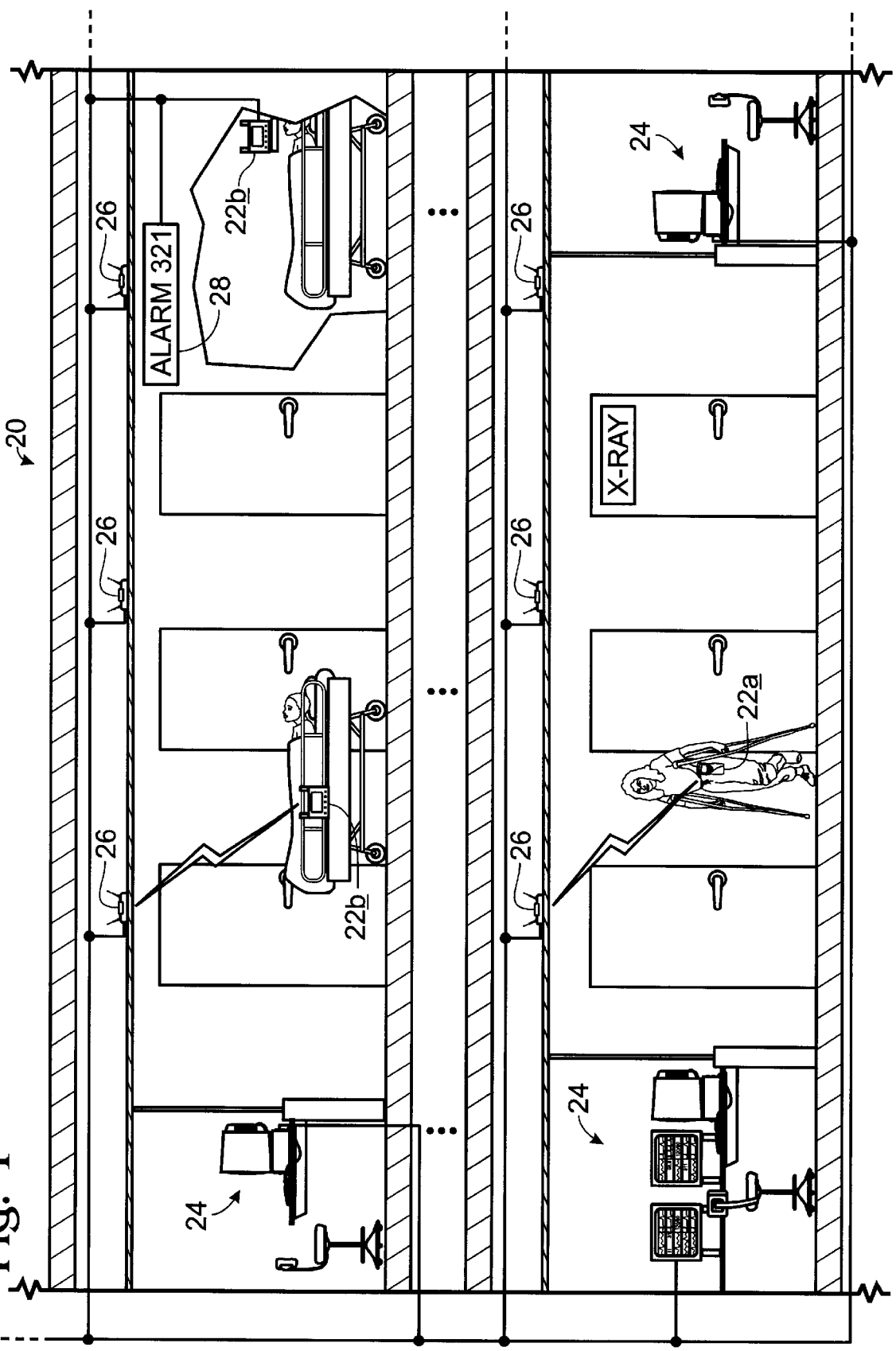
FIG. 1 is a fragmentary, schematic illustration of an exemplary medical telemetry network according to the present invention in the context of a hospital.

Turning now to details, a system for monitoring patients according to the present invention is indicated generally at 20 in FIG. 1. System 20 includes one or more patient monitors 22, each adapted to collect vital signs data from a patient. System 20 also includes one or more central monitoring stations 24 adapted to communicate with the patient monitors and receive, process and store the vital signs data. Thus, physicians, nurses and other health-care personnel (hereinafter referred to collectively as clinicians) are able to monitor a plurality of patients simultaneously and continuously from one or more central locations. As will be described in more detail below, patient monitors 22 and central stations 24 are coupled to communicate using wireless transmissions within a medical telemetry network, thereby allowing a patient to move about inside or outside a monitoring facility without loss of central monitoring.

In the exemplary embodiments shown and described herein, system 20 is configured for use in a hospital. However, it will be appreciated that system 20 also may be used in a variety of other environments including: (i) other types of medical facilities, research facilities, senior-care facilities, hospices, field hospitals, etc.; and (ii) types of non-medical facilities and environments such as patient residences, retail stores, or patient locations outdoors. Therefore, it will be understood that the description herein encompasses medical telemetry systems for use in all such environments.

System 20 may be configured to provide patient monitoring within selected regions of a facility or throughout the facility. In the exemplary embodiment depicted in FIG. 1, system 20 is configured with patient monitors and central stations on multiple floors of a hospital. System 20 includes one or more wireless transceivers 26 disposed within the facility and configured to communicate with patient monitors 22 via wireless transmissions. The wireless transceivers are configured to convey communications between the patient monitors and the central stations. As a result, centralized patient monitoring will extend wherever wireless transceivers 26 are disposed within a facility.

Transceivers 26 may be also be characterized as transmitter/receivers 26, i.e. any device capable of transmitting and sending communication signals, whether it be a device operable for a wired application or a device operable for a wireless application. However, for purposes of the remainder of the description of the exemplary embodiment, the term transceivers will be used to describe for the wireless application being described.

Each floor may include a single central station (as shown on the upper floor in FIG. 1) or plural central stations (as shown on the lower floor). Alternatively, a single central station may be configured to monitor patients on multiple floors. In many hospitals, central stations 24 are assigned to sections within the hospital that perform different functions rather than to particular floors. For example, one or more central stations may be configured to monitor patients admitted to the Intensive Care Ward, one or more different central stations may be configured to monitor patients admitted to the Emergency Room, while one or more other central stations may be configured to monitor patients admitted to the Maternity Ward, etc. Regardless of how the central stations are arranged or assigned, system 20 may be configured to allow any patient monitor 22 to be monitored by any central station 24.

In addition to allowing multiple remote patients to be monitored at a central location, system 20 may also be configured to allow clinicians to view information about a patient's condition from various locations inside and/or outside the hospital. For example, in the embodiment depicted in FIG. 1, system 20 includes one or more annunciating devices 28, each having a display adapted to identify a particular patient (e.g., by name, room number, etc.) and to provide some information concerning the patient's condition. Typically, annunciating devices 28 are used to indicate alarm conditions for a monitored patient. Alternatively, the annunciating devices may be configured to indicate the condition of selected patients regardless of whether an alarm condition exists. In addition to annunciator devices 28, system 20 may also include other devices configured to enable clinicians to monitor a patient's condition at a location remote from either the patient or the central station. These other devices will be described in more detail below.

System 20 may be implemented in many different forms and configurations using various types and combinations of components to provide a variety of features and functions within the scope of the invention. For clarity, the invention will be described below primarily in the context of one particular exemplary embodiment. However, it will be understood that the scope of the invention is not limited to the particular embodiment described, but rather extends to all such embodiments, forms, configurations, types and combinations.

Figure 2:
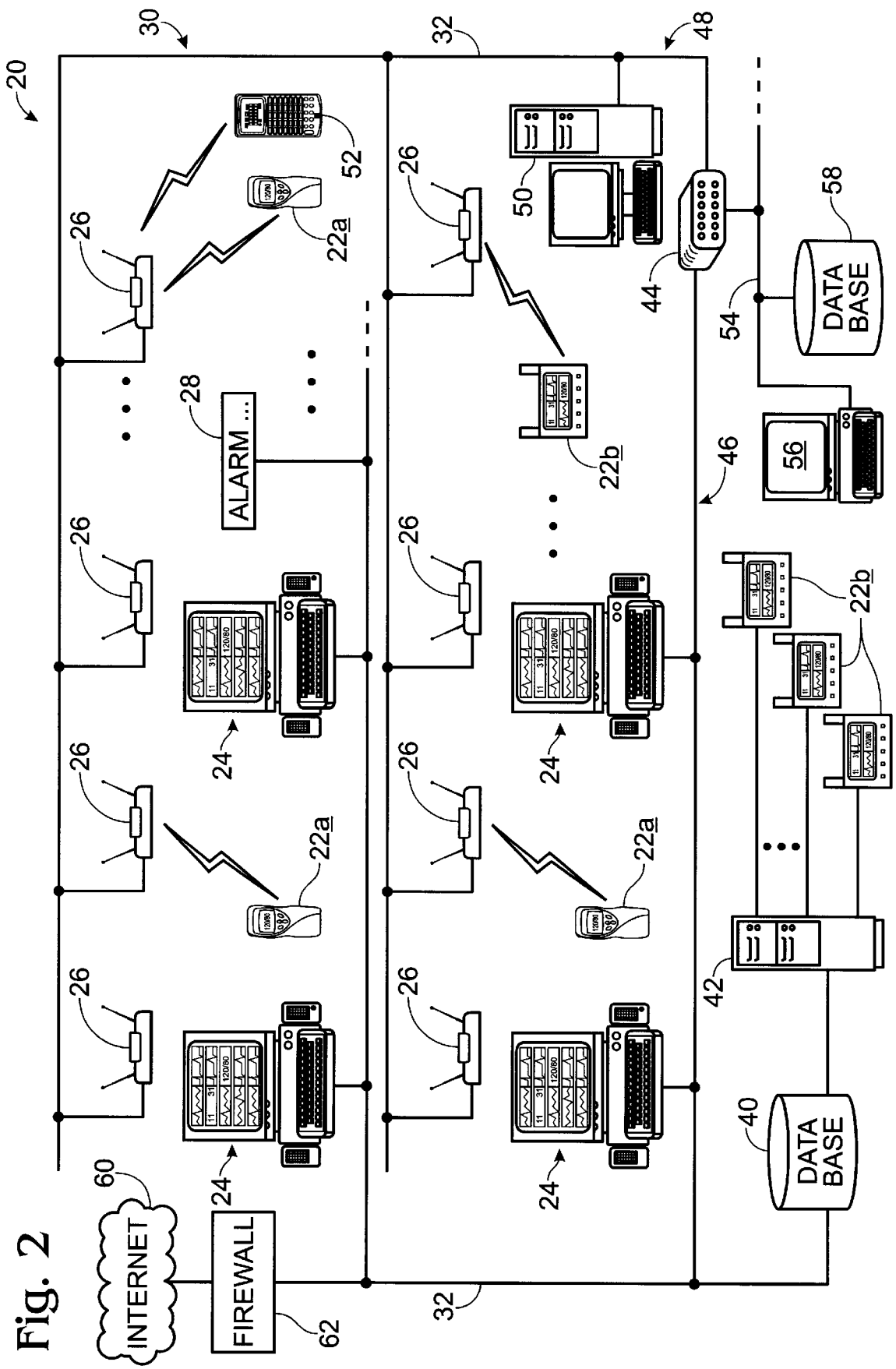
FIG. 2 is a fragmentary, schematic diagram of a system for monitoring a plurality of patients in accordance with the present invention.

Turning attention to FIG. 2, a schematic representation of exemplary system 20 is shown. The system includes a medical telemetry network 30 adapted to monitor a plurality of patients. In the exemplary embodiment, network 30 includes a physical data transport structure 32 (also referred to herein as a network) such as an Ethernet Local Area Network (LAN) system. Alternatively, network 30 may be any of the electrical and/or optical network communications structures known to those of skill in the art. Alternatively, physical data transport structure 32 may include any other suitable network structure, including a wireless structure, whether now known or later developed. In any event, physical data transport structure 32 is adapted to interconnect a plurality of network components, and to transmit data communications between the components.

Although not shown in FIG. 2, it will be appreciated by those of skill in the art that physical data transport structure 32 typically will include one or more devices adapted to connect the physical transmission lines together and route communications within the communications structure. Examples of such devices include switches, hubs, bridges, routers, and the like. Thus, as used her herein physical data transport structure 32 includes all such devices which may be necessary and/or beneficial to a particular implementation as well as the physical communication lines.

Communications transmitted within network 30 typically comply with one or more standard data communication protocols which are known to those of skill in the art. As will be described in more detail below, the components of exemplary network 30 use a variety of standard communication protocols including the Transmission Control Protocol/Internet Protocol (TCP/IP) suite, User Datagram Protocol (UDP), etc. Use of standard communication protocols allows a variety of different components to be connected to communicate over the network. Furthermore, use of standard communication protocols enables the use of standard routers, switches and other network devices as mentioned above. Alternatively or additionally, the components may communicate using one or more non-standardized protocols adapted for medical telemetry or a particular application.

Network 30 includes one or more central stations 24, each connected to communicate via physical data transport structure 32 and configured to monitor a plurality of patients. It will be appreciated that central stations 24 may take any one or more of a variety of different forms. In the exemplary embodiment, each central station takes the form of a computer workstation configured to communicate via physical data transport structure 32 and monitor a plurality of patients. Central stations 24 may be any suitable type of central station such as the ACUITY® central station available from Welch Allyn Protocol, Inc. of Beaverton, Oreg. The ACUITY® central station is a version of the invention claimed in U.S. Pat. No. 5,319,363 to Welch et al.

Figure 3:
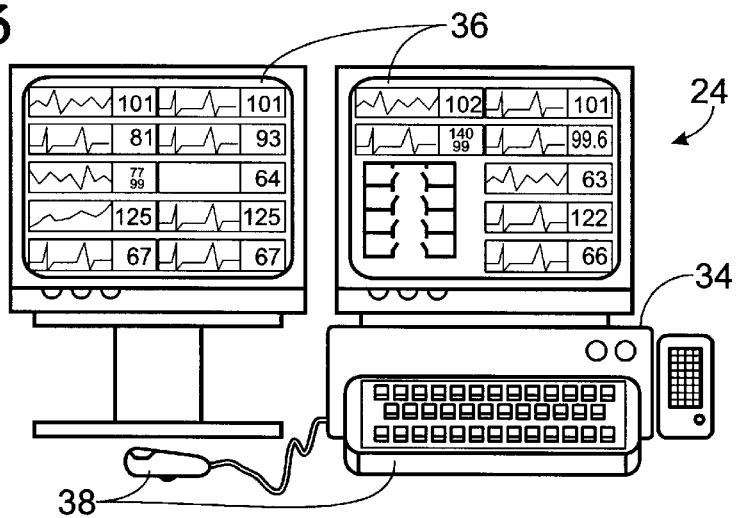
FIG. 3 is a front elevation view of an exemplary central monitoring station according to the present invention.

One example of a central station in accordance with the present invention is shown in FIG. 3. Exemplary central station 24 includes a processing module 34 having at least one processor (not shown) and at least one data storage unit (not shown). The processor is adapted to execute software stored in the data storage unit to communicate with patient monitors, analyze patient data, etc. Central station 24 also includes a plurality of display devices such as display monitors 36. Alternatively, central station 24 may include a single display monitor. In any event, display monitors 36 are connected to processing module 34 and adapted to display vital signs data collected from a plurality of patients. Typically, central station 24 also includes one or more input devices 38 (e.g. keyboard, cursor control, mouse, remote control, touch-screen, etc.) operable by a user to control the central station. Central station 24 may also include one or more audio input/output (i/o) devices such as speakers, microphones, sirens, buzzers, etc., adapted to produce an audible message to a user of the central station n. Those of skill in the art will appreciate that central stations 24 may have a variety of different configurations within the scope of the invention.

Central stations 24 are typically disposed at selected centralized locations within the hospital such as at nursing stations, etc. Each central station is adapted to receive patient vital signs data from one or more patient monitors via physical data transport structure 32. The central stations are controllable by a user to display selected information concerning each monitored patient on the display monitor. This allows clinicians to view the information collected by a patient monitor at the centralized location. Additionally, central stations 24 may be configured to simultaneously display data from a plurality of patients, thereby enabling a single clinician to watch over several patients at different locations. In addition to communicating with patient monitors, central stations 24 may also be configured to communicate with other central stations within the network. Thus, for example, patient data received at one central station may be forwarded to a different central station. This allows two or more clinicians at different locations to simultaneously monitor a single patient. Communications among different central stations will be described in more detail below.

Turning attention back to FIG. 2, network 30 may also include one or more database systems 40 configured to store patient information. Database system 40 is connected to physical data transport structure 32 and accessible by central stations 24 to store and retrieve data. Patient information stored on database system 40 may include a variety of information concerning each patient including personal information, medical history, room location, etc. Typically, the central stations are configured to access database system 40 to identify patients who are admitted to the hospital and display a list of the patients on display monitor 36. This allows a clinician to associate vital signs data received from a particular patient monitor with the corresponding patient. The central station also may be configured to store on database system 40 some or all of the vital signs data received from the patient monitors. While database system 40 is depicted in FIG. 2 as a single, separate system connected to physical data transport structure 32, it will be appreciated that other configurations are also within the scope of the invention. For example, database system 40 may be multiple databases distributed around network 30. Alternatively, database system 40 may be contained within some or all of the central stations. Typically, database system 40 is a system or network of data storage devices, some of which are contained within the central stations and others existing separately in network 30. In any event, it will be appreciated that database system 40 may be any of the various database systems or structures such as are known to those of skill in the art.

As discussed above, central stations 24 are configured to communicate with a plurality of patient monitors via physical data transport structure 32. Communications between the central stations and patient monitors may be via wire (i.e., transmitted over a physical line adapted to convey electrical or optical signals), or may be wireless communications. Considering first the wire communications, one or more patient monitors 22 may be connected to physical data transport structure 32 either directly (e.g., through an Ethernet connection), or indirectly through a terminal server 42 or similar device. Terminal server 42 includes a plurality of ports adapted to receive connections from the patient monitors. In addition, the terminal server is also connected to physical data transport structure 32. The terminal server is configured to receive communications from the patient monitors and forward the communications to the appropriate central station via physical data transport structure 32. Similarly, the terminal server also is configured to receive communications from the central stations via physical data transport structure 32 and convey the communications to the appropriate patient monitor. Terminal server 42 may be any of a variety of terminal servers such as are known to those of skill in the art. Any known wire or wireless communication technologies may be used to perform the functions described above.

In TCP/IP based networks, communications between central stations and patient monitors are directed to the appropriate component using network addresses such as IP addresses as well as hardware addresses. Typically, each central station is assigned a unique IP address and all communications to and from a particular central station will include the particular station's IP address. Similarly, all patient monitors which are directly connected to physical data transport structure 32 are assigned a unique IP address. In contrast, patient monitors which are connected to physical data transport structure 32 through a terminal server typically do not have a unique IP address. Instead, the terminal server has an IP address with which to communicate with the other components connected to physical data transport structure 32. Communications from a patient monitor are transmitted to the terminal server with the IP address of the destination component (e.g., a central station). The terminal server appends its own IP address to each communication and then forwards the communication to the appropriate component. Similarly, communications to a patient monitor are transmitted with the terminal server's address as the destination address. Upon receipt, the terminal server forwards the communications to the appropriate patient monitor.

As shown in FIG. 2, network 30 also includes one or more wireless transceivers 26, which are hereinafter referred to as access points 26. Each access point is connected to physical data transport structure 32 and configured to communicate with the other components connected to physical data transport structure 32. Each access point includes the software necessary to communicate via physical data transport structure 32 using the selected communications protocols of network 30 (e.g., TCP/IP, UDP, etc.). In the exemplary embodiment, each access point has a unique IP address that may be permanently coded into the access point, or may be assigned by a server such as described below. The access points also are configured to communicate, via wireless transmissions, with components which are not directly connected to physical data transport structure 32. Each access point includes a wireless receiver to receive wireless communications, and a wireless transmitter to transmit wireless communications.

It will be appreciated that access points 26 may be configured to communicate using any of a variety of different wireless transmission technologies depending on the application, environment, governmental regulations, etc. In the exemplary implementation, the access points are configured to communicate with the patient monitors (described in more detail below) as well as other devices under the IEEE 802.11 standard using Frequency Hopping Spread Spectrum (FHSS) technology in the 2.4 GHz ISM (Industrial, Scientific, and Medical) band. The IEEE 802.11 communications standard is well known to those of skill in the art. Access points 26 essentially act as network bridges between the wireless components of network 30 and wired network physical data transport structure 32. Other wireless transmission, or communication, technologies known to those skilled in the art may be used including IEEE 802.11a, IEEE 802.11b, and IEEE 802.15.

Exemplary access points 26 may be any wireless transceivers adapted to communicate using the IEEE 802.11 FHSS technology. One example of a suitable access point is the SPECTRUM24 AP 3021 available from Symbol Technologies of Holtsville, N.Y. In other implementations and embodiments, access points 26 may be selected which are configured to communicate using other technologies. In any event, the access points usually are configured to simultaneously communicate with a plurality of patient monitors and/or other wireless devices. For example, the AP 3021 access points are adapted to simultaneously communicate with up to approximately 15 patient monitors.

Each access point typically has a range within which it can communicate with wireless devices. The range will vary depending on the power of the wireless transmitter, environmental conditions, etc. Typically, the access points are arranged within the hospital so that at least one access point is able to communicate with a patient monitor at any point within a defined region of the hospital. For example, if it is desired that wireless patient monitors be used on a particular floor of the hospital, then sufficient access points are provided and positioned so that every location on the particular floor is within the range of one or more access points. This ensures that a patient associated with a patient monitor can move about the hospital floor without loss of central monitoring. It will be understood that the access points may be arranged to provide wireless coverage within a defined region that is less than an entire floor of the hospital. Alternatively, the access points may be arranged to provide coverage for regions that span multiple floors (whether or not adjacent) and/or multiple buildings.

As will be discussed in more detail below, patient monitors and other wireless devices communicate over physical data transport structure 32 by first associating with an access point. Once a patient monitor has associated with a particular access point, communications between the patient monitor and components on physical data transport structure 32 are conveyed by the particular access point. However, as the patient monitor moves out of range of the particular access point and into the range of another access point, the patient monitor associates with the other access point and subsequent communications between the patient monitor and components on physical data transport structure 32 are conveyed by the other access point.

Use of FHSS technology allows access points to be positioned so that the ranges of the access points overlap. Such an arrangement provides for geographic redundancy in the event an access point fails. In addition, overlapping the access point ranges increases the monitoring capacity within the defined region or selected portions of the defined region. The access points typically are configured to communicate with one another to minimize or prevent interference. The access points may also be configured to manage and balance the communication loads experienced by each access point. In addition, one or more of the central stations may be configured to control the access points to balance communication loads.

It will be appreciated that in many implementations the communication of patient information by wireless transmission must be secure and confidential. These security needs may be met in any of a variety of ways known to those of skill in the art. For example, the 802.11 standard provides WEP (Wired Equivalent Privacy) which encrypts the wireless transmissions. In addition, some implementations may utilize additional security measures such as end-to-end data encryption, etc.

In the exemplary embodiment, network 30 also includes a router 44 or similar device connected to physical data transport structure 32 between a first portion 46 and a second portion 48 of physical data transport structure 32. Components connected to the first portion are assigned IP addresses corresponding to a first subnet, while components connected to the second portion are assigned IP addresses corresponding to a second subnet. First portion 46 is connected to central stations 24, database system 40, terminal server 42 and the other components of network 30 which are configured for wired communications via physical data transport structure 32. Second portion 48 is connected to access points 26. Thus, first portion 46 may be seen as a wired portion of network 30, while second portion 48 may be seen as a wireless portion of network 30. Use of router 44 between wired portion 46 and wireless portion 48 allows the wireless portion of the network to be isolated from the communication traffic on the wired portion of the network. Communications between patient monitors and central stations are passed by router 44 from wired portion 46 to wireless portion 48 and vice versa. However, communications between central stations and/or other components connected to wired portion 46 are not passed to wireless portion 48. Alternatively, wired portion 46 and wireless portion 48 may be directly connected to the same subnet, eliminating the need for a router.

In the exemplary embodiment, network 30 also includes at least one server system 50 connected to the wireless portion of the network. As will be discussed in more detail below, server system 50 is adapted to assign IP addresses to the patient monitors once the patient monitors associate with an access point. Server system 50 may be configured to assign IP addresses according to any suitable protocol such as the Dynamic Host Configuration Protocol (DHCP), the Bootstrap Protocol (BOOTP), etc. It will be appreciated that server system 50 is connected on the wireless portion of physical data transport structure 32 relative to router 44 to ensure that requests for IP addresses from the patient monitors are received at server system 50. Alternatively, router 44 may be configured to convey the requests for IP addresses between the wireless and wired portions, in which case server system 50 may be connected on the wired portion of the network.

Server system 50 may be a separate computer system adapted to manage and assign IP addresses only, or it may be configured to perform other functions including network management, etc. In alternative embodiments, one of central stations 24 is configured to perform the functions of server system 50, thereby alleviating the need for a separate server system 50. In such embodiments, the central station which is configured to assign IP addresses in the alternative embodiment should be connected to the wireless portion of network 30 unless router 44 is adapted to pass requests for an IP address to the wired portion of the network.

Network 30 may also include one or more wireless communication devices referred to herein as clinician terminals 52. The wireless clinician terminals may take any one of a variety of different forms including Personal Digital Assistants (PDA's), Internet Protocol (IP) telephones, portable computers, etc. Clinician terminals 52 include wireless transceivers (e.g., RF network cards) that are configured to associate with access points 26. The clinician terminals also include suitable software executable by the terminals to communicate with the central stations via access points 26. The clinician terminals may also be configured to perform a variety of functions such as receiving and displaying patient vital signs data from the central station, transmitting control instructions to the central station to control a selected aspect of the central station, transmitting control instructions to the central station for forwarding to a patient monitor to control selected aspects of the patient monitor, sending and receiving textual messages, receiving and acknowledging alarm signals, etc. In the exemplary embodiment, clinician terminals 52 are configured to function as quasi-central stations, by displaying patient vital signs data and providing a user-interface operable by the clinician to control the patient monitor.

Clinician terminals 52 enable physicians, nurses and others to obtain information concerning a patient from any location within the defined region of network 30, rather than only at the patient's location or at a central station. Thus, for example, a clinician several floors away from a patient can receive a notification of an alarm at the patient monitor associated with the patient. Further, the clinician can evaluate the patient's condition from the vital signs data without going to the patient's location. The clinician may then take appropriate action depending on the patient's condition. It will be appreciated that clinician terminals 52 enable clinicians to work more efficiently and effectively, and to care for a larger number of patients than would otherwise be possible. Furthermore, while the clinician terminals may include paging functions, the clinician terminals provide substantially more information to the clinicians than pagers.

Exemplary telemetry network 30 also is connected to the main computer network 54 of the hospital, referred to hereinafter as the secondary or non-telemetry network. Secondary network 54 typically includes a plurality of computer terminals 56, database systems 58, etc. The secondary network interconnects the hospital's administrative computers and other non-telemetry components. Typically, secondary network 54 is connected to telemetry network 30 through router 44. This isolates the telemetry network from non-telemetry communication traffic, while allowing devices connected to the non-telemetry network to access patient vital signs data. Similarly, users of central stations 24 are able to access information on the secondary network as needed. In some implementations it may be desirable to provide security measures to ensure that only authorized users of secondary network 54 are able to access telemetry network 30. Any of a variety of suitable security measures may be employed as are known to those of skill in the art.

Network 30 may also be connected to a communications network external to the hospital such as an extranet, virtual private network, Wide Area Network (WAN), etc. In the exemplary implementation, network 30 is connected to the Internet 60. Typically, network 30 is connected to the Internet via a firewall 62 or other suitable security device to restrict access to patient data and other confidential information.

Figure 4:
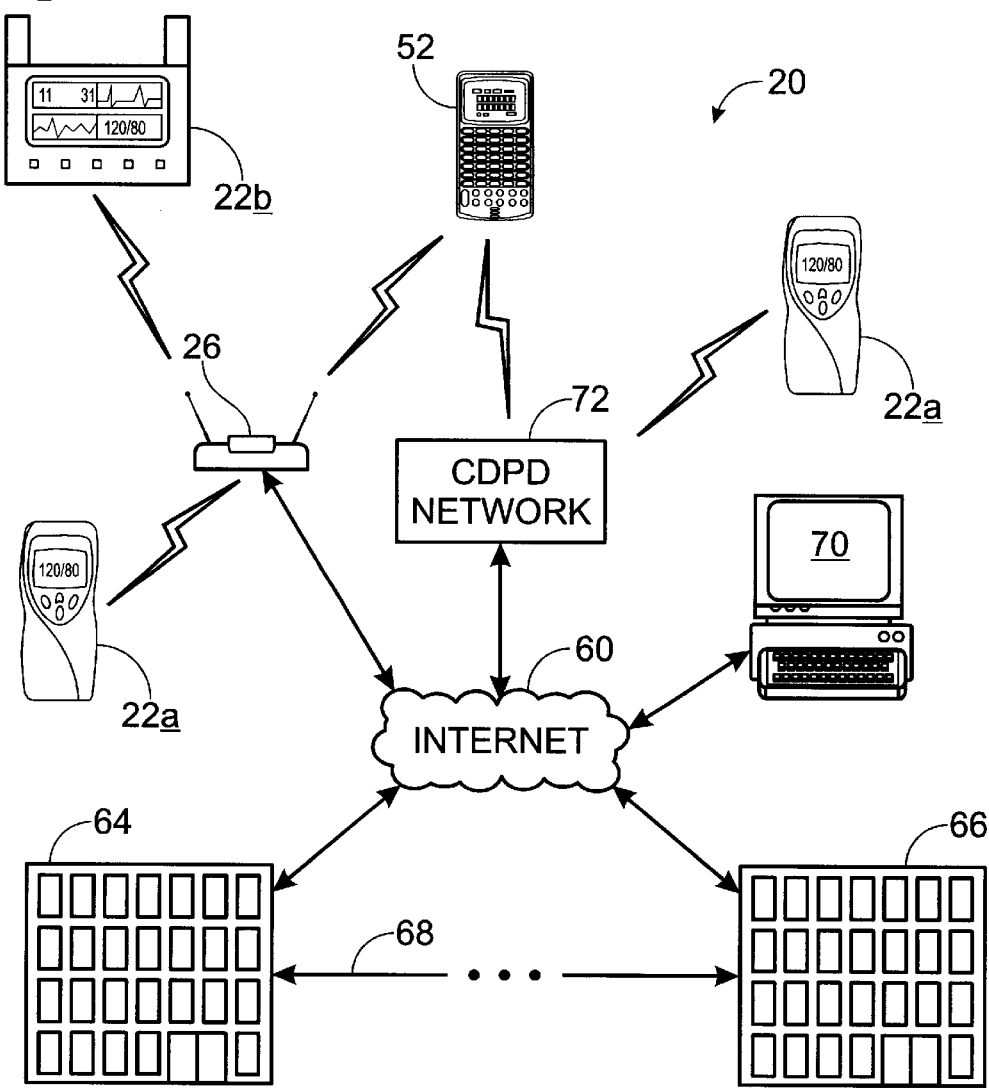
FIG. 4 is a schematic diagram of an exemplary system for monitoring patients according to the present invention.

As shown in FIG. 4, the telemetry network of one hospital 64 may be connected to the telemetry network and/or the secondary network of one or more other hospitals 66 in remote locations. The telemetry network may be connected to the remote hospitals via Internet 60 or via a direct, non-public network 68 such as is known to those of skill in the art. Central stations 24 of hospital 64 may be configured to transmit patient information including vital signs data to central stations or other computers in remote hospital 66. Similarly, the central stations of hospital 64 may be configured to request and receive patient information including vital signs data from remote hospitals 66. It will be appreciated that communication of patient information between remote hospitals allows clinicians to participate in consultations with their remote colleagues more effectively and efficiently.

In the implementation described above, access points 26 were arranged within the hospital to provide wireless monitoring in a defined region of the hospital. In alternative implementations, the defined region may extend outside the hospital. For example, system 20 may include one or more access points 26 which are positioned outside of the hospital, as shown in FIG. 4. The access points are connected to Internet 60 and configured to transmit the patient vital signs data to network 30 and one or more central stations 24. This allows patients to move outside of the hospital without loss of continuous central monitoring. So long as the patient remains within the range of at least one access point, the patient's vital signs data may be displayed on a central station as if the patient was still in the hospital. Similarly, emergency response workers could connect a patient monitor to an accident victim so that the hospital can monitor the victim's condition while the victim is transported to the hospital.

It will be appreciated that placement of access points outside of the hospital also allows clinicians to access patient data when outside the hospital. As shown in FIG. 4, one or more clinician terminals 52 may associate with the external access points to view patient information and control the patient monitor connected to a patient. This provides clinicians with more flexibility to leave the hospital while continuing to monitor their patients at the hospital (or patients outside the hospital). Alternatively, clinicians may monitor patients using personal computers 70 or similar devices configured to connect to Internet 60 and communicate with central stations at the hospital. Computers 70 may be located anywhere a connection is available that provides a communication channel using any communication technology. For example, computers 70 may be located anywhere a connection to the Internet is available. Alternatively, computers 70 may be configured to associate with an external access point and communicate via wireless transmissions.

As discussed above, the defined region of monitoring will extend outside the hospital wherever access points 26 are positioned. In areas where the external network of access points is undeveloped, patient monitors 22 and/or clinician terminals 52 may be configured to communicate using other wireless communication technologies. For example, the implementation depicted in FIG. 4 includes a Cellular Digital Packet Data (CDPD) network 72, such as is currently used for cellular telephone and other communications. Patient monitors 22 and/or clinician terminals 52 may be configured to communicate with central stations in hospital 64 via CDPD network 72. Thus, for example, a patient might be discharged to go home while continuing to be monitored. It will be appreciated that this alleviates the need to have new wireless networks installed throughout a geographic region, since the components of system 20 are configured to communicate using preexisting networks. An alternate implementation (undepicted) would be to use what is known as a Global System Mobile (GSM), or any other available wide-reaching communication system.

Considering patient monitors 22 in more detail, it will be appreciated that there are a variety of different patient monitors available and suitable for use with system 20. System 20 may include one or more patient monitors of a single type, or may include multiple types of patient monitors, each configured to communicate with one or more central stations. For example, the exemplary embodiment of system 20 depicted in FIGS. 1 and 2 includes a first type of patient monitor 22a adapted to be carried or worn by a patient, and a second type of patient monitor 22b adapted to be mounted on a bed, wheelchair, etc, as well as being carried. Patient monitors 22a and 22b may be configured to perform the same monitoring functions or may be configured to perform different monitoring functions. In any event, each type of patient monitor 22 is configured to collect vital signs data from a patient and communicate at least a portion of the vital signs data to a central station via physical data transport structure 32. Suitable patient monitors are available from several manufacturers, including the MICROPAQ and PROPAQ patient monitors available from Welch Allyn Protocol, Inc. of Beaverton, Oreg.

Figure 5:
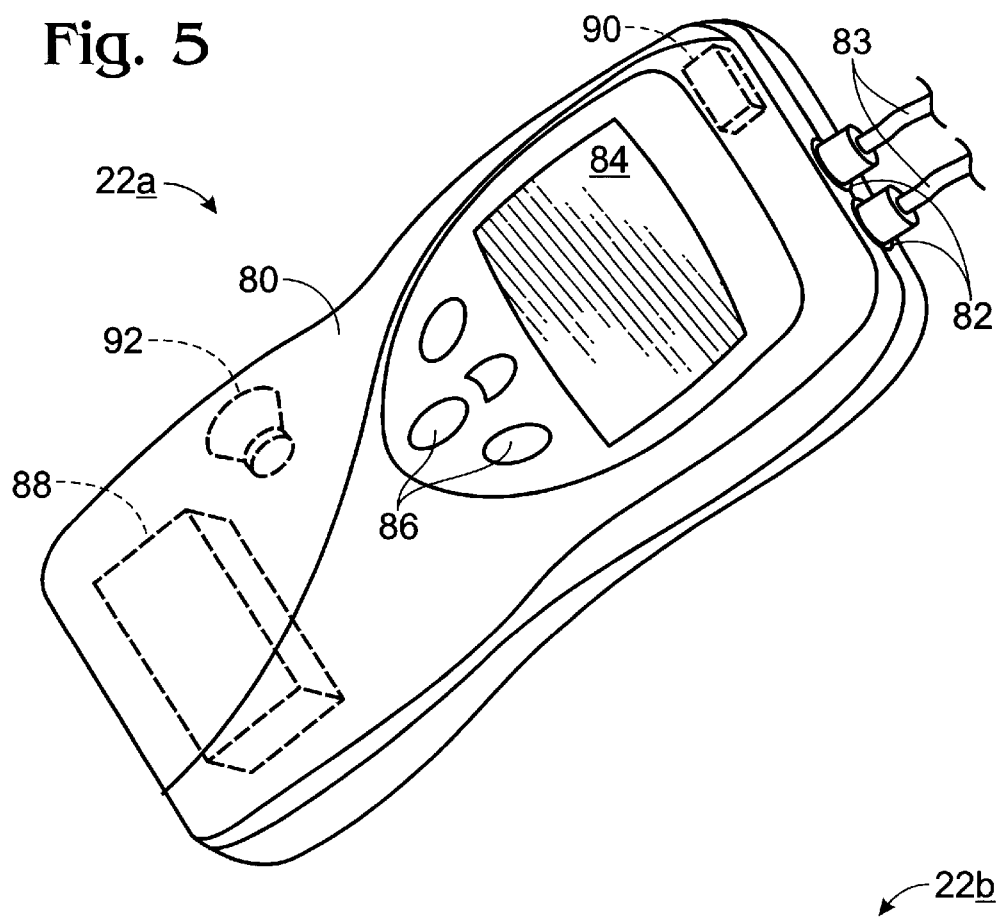
FIG. 5 is a front isometric view of an exemplary patient monitor according to the present invention.

Turning attention now to FIG. 5, exemplary patient monitor 22a is shown in more detail. The monitor includes a portable housing 80 having one or more sensor input ports 82. The housing is sized to be held by a clinician or patient, or to be worn by the patient using a strap, belt, or similar device. Sensor input ports 82 are adapted to receive and connect to sensor cables 83. Each cable 83 is attached to one or more sensor assemblies (not shown). The sensor assemblies may include any vital signs sensor assembly adapted to detect and/or measure selected vital signs data from a patient and transmit the vital signs data via cables 83. Examples, of suitable sensor assemblies include electrocardiogram (ECG) sensor assemblies, non-invasive blood pressure sensor assemblies, invasive blood pressure sensor assemblies, temperature sensor assemblies, pulse oximetry sensor assemblies, respiration sensor assemblies, carbon dioxide sensor assemblies, etc. Suitable sensor assemblies are available from Welch Allyn Protocol, Inc. of Beaverton, Oreg. In any event, each sensor input port is adapted to receive patient vital signs data from the sensor assembly attached thereto.

Patient monitor 22a also includes a display device such as display screen 84 adapted to display the vital signs data or an image representative of the vital signs data. Exemplary display screen 84 is in the form of a liquid crystal display (LCD) device. Alternatively or additionally to display screen 84, patient monitor 22a may include any other suitable display device such as a printer, one or more indicator lights, light-emitting diodes, etc. The patient monitor also includes one or more input devices such as buttons 86 disposed on housing 80. Buttons 86 are operable by a user to input information into patient monitor 22a, as will be discussed in more detail below. In addition to, or in place of buttons 86, the patient monitor may include other types of input devices including switches, knobs, etc. As a further alternative, display screen 84 may be a touch-screen adapted to input information in response to contact by the user at selected locations on the screen. While the exemplary embodiment will be described below as having input devices in the form of buttons, it will be understood that any type of input device may be used.

Exemplary patient monitor 22a further includes a battery assembly 88 having one or more batteries. Battery assembly 88 is mountable in a battery compartment within housing 80. The batteries typically are rechargeable, however non-rechargeable batteries may also be used. Although not shown in FIG. 5, patient monitor 22a also includes a controller, a memory device, and an on-board wireless transceiver, all operably disposed within portable housing 80. An internal antenna 90 is mounted within the housing and coupled to the wireless transceiver. Alternatively, antenna 90 may be disposed externally to housing 80. An audio input/output device 92, (e.g., speaker, microphone, buzzer, siren, etc.) is also disposed within the housing and adapted to produce an audible notification to a clinician, patient, or other user of the monitor. An alternative to the input/output device would be a bi-directional audio device.

Figure 6:
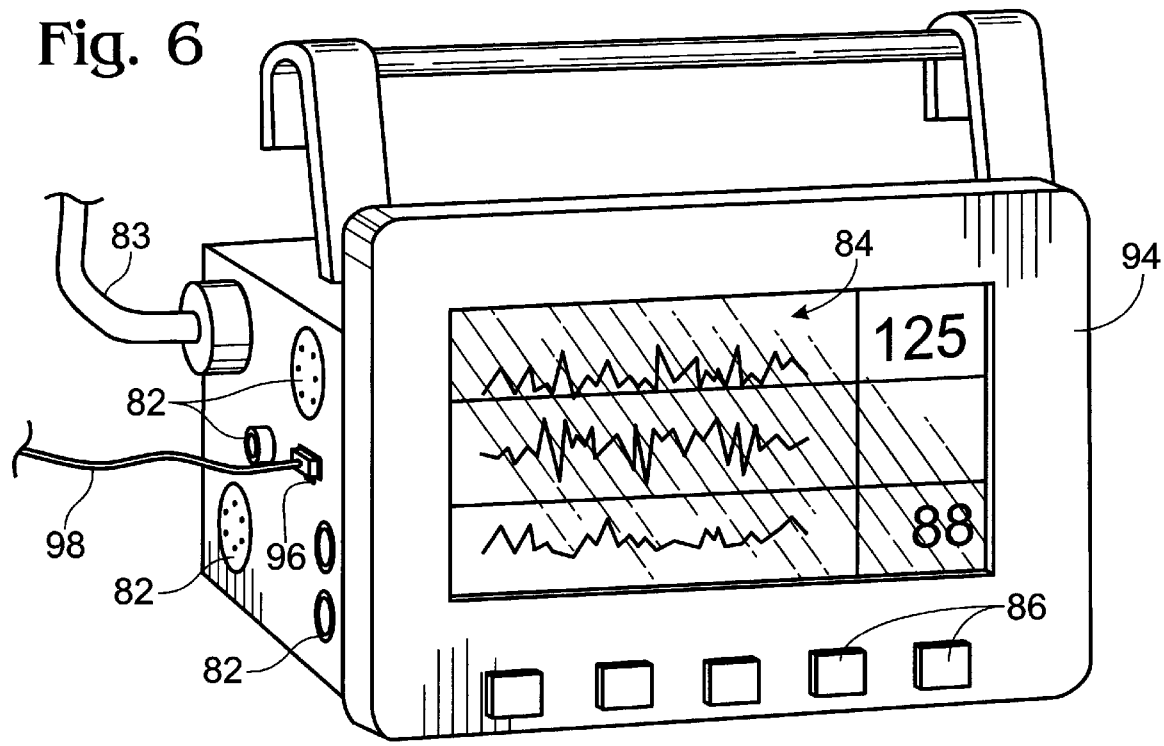
FIG. 6 is a front isometric view of another exemplary patient monitor according to the present invention.

As shown in FIG. 6, exemplary patient monitor 22b includes a portable housing 94 adapted to attach to a bed, wheelchair or other support structure. Housing 94 includes one or more sensor input ports 82 adapted to connect to sensor cables 83 and receive vital signs data from one or more sensor assemblies (not shown). Similar to patient monitor 22a, patient monitor 22b includes a display device such as display screen 84 and one or more input devices such as buttons 86. Although not shown in FIG. 6, patient monitor 22b also includes a battery assembly 88, an antenna 90, and an audio output device 92. As will be described in more detail below, patient monitor 22b also includes a controller, a memory device and an on-board wireless transceiver, all operably disposed in housing 94.

Unlike patient monitor 22a, patient monitor 22b includes an output port 96 adapted to receive a hard-wired network connection cable 98 such as an Ethernet, RS-232, modem line, or similar network communications cable for connection to physical data transport structure 32 or terminal server 42. Thus, patient monitor 22b is configured to communicate with central stations 24 using either wireless communications via its on-board wireless transceiver, or wire communications via output port 96. As will be discussed in more detail below, patient monitor 22b may be configured to automatically switch between wire and wireless communications in various situations.

Figure 7:
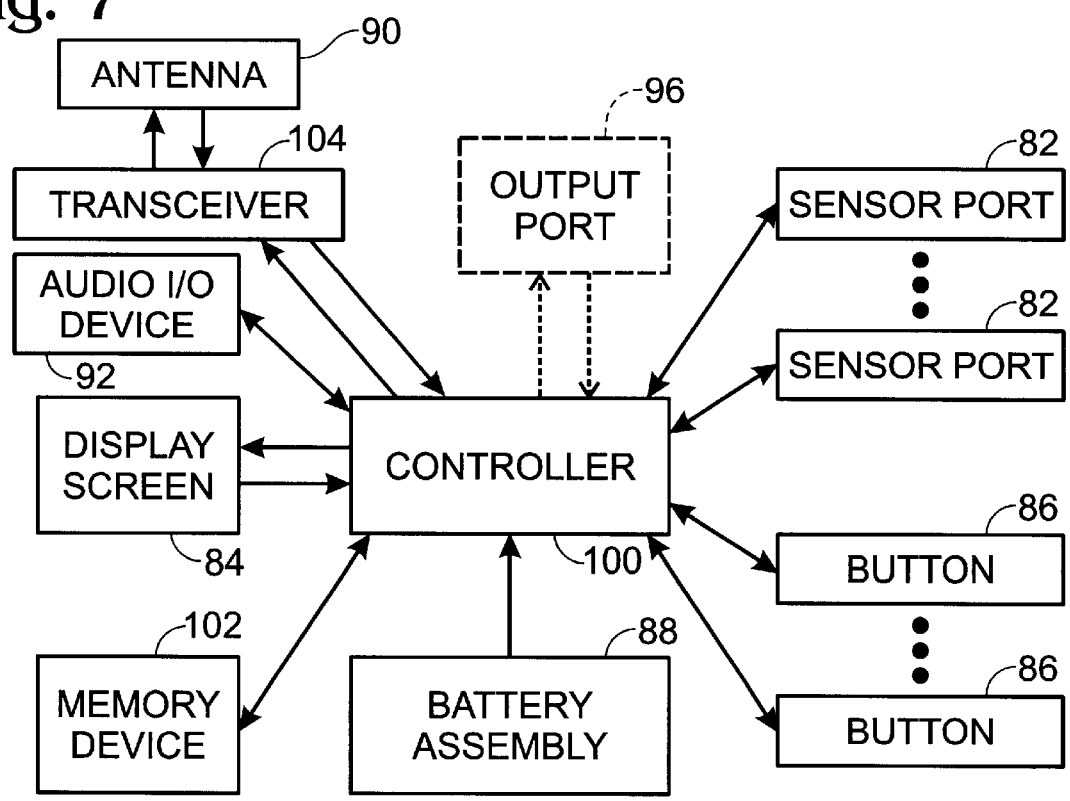
FIG. 7 is a schematic, functional block diagram of an exemplary patient monitor according to the present invention.

As mentioned above, each patient monitor 22 includes a controller disposed within the portable housing. It will be appreciated that any of a variety of different computer controllers, micro-controllers, or processors, such as are known to those of skill in the art, may be used. The controller, indicated at 100 in FIG. 7, is operably coupled to receive power from battery assembly 88. The controller may also be configured to receive power from other sources (e.g., AC line current through a wall socket, DC current through photovoltaic cells, etc.).

Controller 100 is also connected to memory device 102. It will be appreciated that memory device 102 may be any one or a combination of devices adapted to store electronic information such as RAM, ROM, PROM, EPROM, etc. Memory device 102 may also include removable storage media such as magnetic discs and tapes, optical discs, etc. In addition to storing patient vital signs data, memory device 102 may be configured to store one or more software control programs executable by controller 100 to perform its various functions including receiving and analyzing vital signs data, presenting information to a user, etc. In addition, the software will include the necessary programs for communicating with central stations 24 (e.g., TCP/IP, DHCP, etc.) While memory device 102 has been depicted as a single device, those of skill in the art will appreciate that memory device 102 may be a plurality of either similar or different memory devices.

Controller 100 is also coupled to sensor ports 82 and configured to receive vital signs data from the sensor assemblies via the sensor ports. In addition, controller 100 may be configured to supply power and/or suitable drive signals onto one or more of the sensor ports to drive the sensor assemblies attached to the ports. In any event, vital signs data received at controller 100 may be stored in memory device 102, processed, discarded, and/or communicated immediately to a central station.

The controller is connected to control wireless transceiver 104 and communicate with central stations 24 via the transceiver. Wireless transceiver 104 may be any of a variety of wireless transceivers which are known to those of skill in the art. One example of a suitable wireless transceiver is the SPECTRUM24 LA 3021 PC card, available from Symbol Technologies of Holtsville, N.Y. Alternatively, other wireless transceivers may be used. In any event, wireless transceiver 104 is configured to communicate with access points 26 using the appropriate communications protocol of network 30. The wireless transceiver is connected to antenna 90 and transmits data received from controller 100 to access points 26. Similarly, the wireless transceiver receives transmissions from one or more access points and forwards the communications to the controller. The wireless communications between patient monitor 22 and the central stations will be discussed in more detail below.

In the case of patient monitor 22b, controller 100 is also connected to output port 96 and configured to communicate with central stations 24 via the output port rather than via wireless transceiver 104. Controller 100 may also include a network card or similar device (not shown) adapted to transmit and receive communications via output port 96. For clarity, the description below assumes that patient monitor 22 communicates with central stations 24 via wireless transceiver 104. However, it will be understood that, unless stated otherwise, and for purposes of this description, communications via output port 96 are viewed as identical to communications via the wireless transceiver, and therefore both types of communications are included within the description. A distinction between wireless and hard-wired communication is that patient location (room) is known with hard-wired communication (via the network jack to which the monitor is connected) and not known with wireless communication. However, for purposes of this description, that distinction is not seen as pertinent and that is why communications via output port 96 are viewed as identical to communications via the wireless transceiver.

Figure 8:
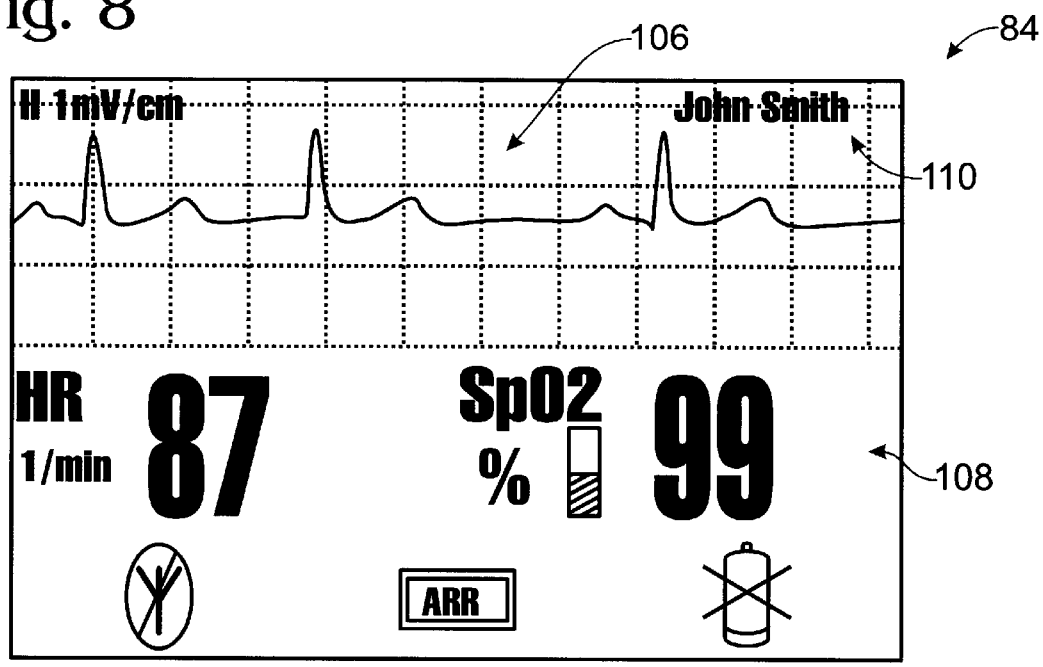
FIG. 8 is an exemplary image for display on a display screen according to the present invention.
Figure 9:
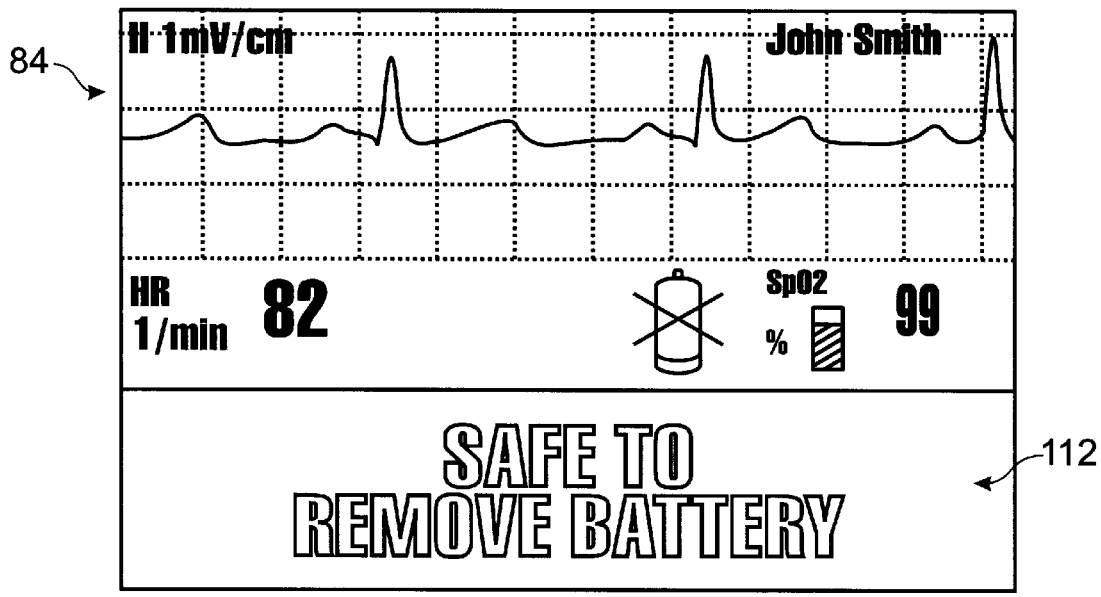
FIG. 9 is similar to the image of FIG. 8 but modified to include a message region for display on a display screen according to the present invention.
Figure 10:
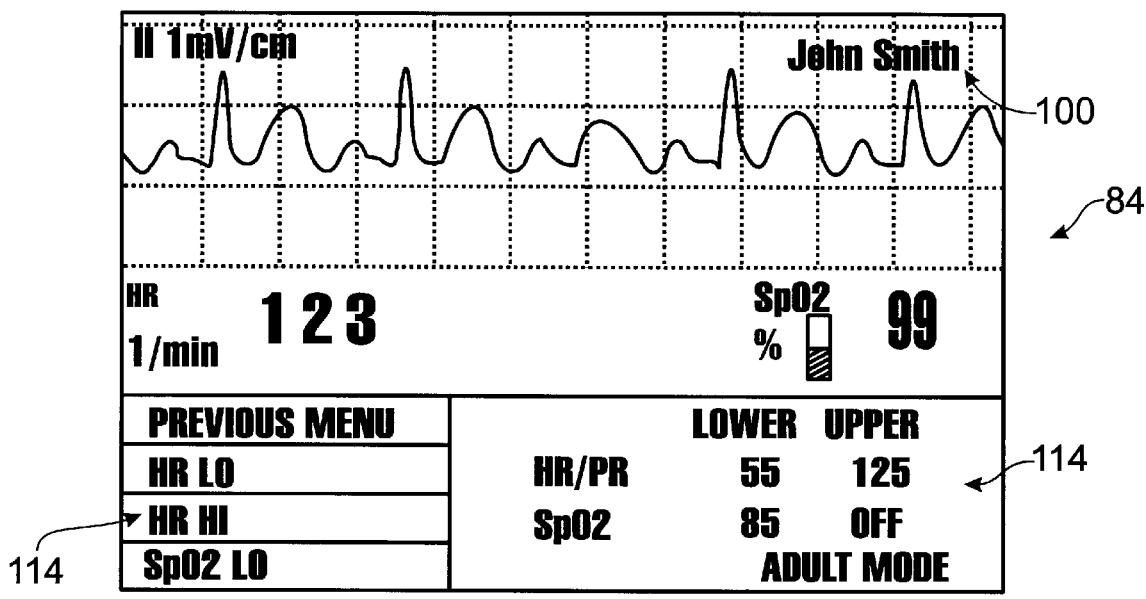
FIG. 10 is similar to the image of FIG. 8 but modified to include a user-interface for display on a display screen according to the present invention.

Controller 100 is also connected to receive inputs from buttons 86. The buttons are operable by a user of the patient monitor to input information to the controller, as well as to control the controller. Each button may have a single function or may have a variety of functions depending on such factors as the operating condition of the controller, status of the sensor assemblies, communications with a central station, screen displays, etc. In the exemplary embodiment, controller 100 is configured to control the function of buttons 86 and to disable the buttons under defined conditions. Controller 100 is configured to control display screen 84 to display an image representing the vital signs data. It will be appreciated that the image displayed on display screen 84 will vary depending on the vital signs data collected by the patient monitor. Additionally, exemplary controller 100 is configured to change the display based on instructions received from the user via buttons 86. For example, the user might select between displaying a single ECG signal from a single electrode, or multiple ECG signals from multiple electrodes. FIG. 8 shows an exemplary display screen 84 on which vital signs data is being displayed. A waveform region 106 of the display shows an image representing the signal data received from an ECG sensor assembly. A numeric region 108 of the display shows images that provide numerical representations of the vital signs data (e.g., heart rate, oxygen saturation in the patient's blood, etc.). The display may also include a patient identifier 110 that uniquely identifies the patient, such as the patient's name, etc. FIG. 9 shows another exemplary display screen 84 similar to the one in FIG. 8. However, the display screen shown in FIG. 9 has been changed to include a message region 112 for displaying messages to a user. Similarly, FIG. 10 shows another exemplary display screen 84 in which the image has been changed to include a user-interface region 114. The user-interface region allows a user to enter information and control the patient monitor by operating buttons 86. Control of the display screen will be described in further detail below.

Controller 100 is also connected to control audio output device 92 and/or other audible indicator devices to produce audible messages or signals. The controller may be configured to control the audio output device to produce audible signals under any one or more of a variety of conditions. For example, controller 100 is typically configured to analyze at least some of the vital signs data and produce an audible alarm if the vital signs data is outside a selected nominal range. The analysis of vital signs data and detection of alarm conditions will be described in further detail below.

While one exemplary functional embodiment of patient monitors 22 has been depicted in FIG. 7 and described above, it will be appreciated that many other configurations are possible. Thus, the invention is not limited to the exemplary embodiment described, but includes any patient monitor configuration adapted to collect vital signs data from a patient and communicate the vital signs data to one or more central stations.

Typically, patient monitors 22 are configured to function as stand-alone devices capable of providing local patient monitoring regardless of whether the patient monitor is in communication with a central station. The patient monitor may be configured to begin monitoring immediately upon power-up and attachment of at least one sensor assembly. Alternatively, the patient monitor may be configured to begin monitoring upon receipt of an actuation signal.

Patient monitors 22 are also configured to attempt to establish communications with one or more central stations and communicate the vital signs data to the central stations. In the exemplary embodiment, the patient monitors are configured to attempt to establish communications immediately at power-up and to continue the attempt until communications are established. Alternatively, one or more of the patient monitors may be configured to attempt to establish communications only in response to an instruction by a user and/or the occurrence of selected conditions. Those of skill in the art will appreciate that the process of establishing communications with one or more central stations, also referred to herein as the rendezvous process, may be carried out in any of a variety of different ways. In addition, the rendezvous process may vary depending on whether the patient monitor is communicating through wireless or wire communications, as well as on whether the patient monitor is establishing a new communications connection or reestablishing prior communications which were lost or terminated.

Figure 11:
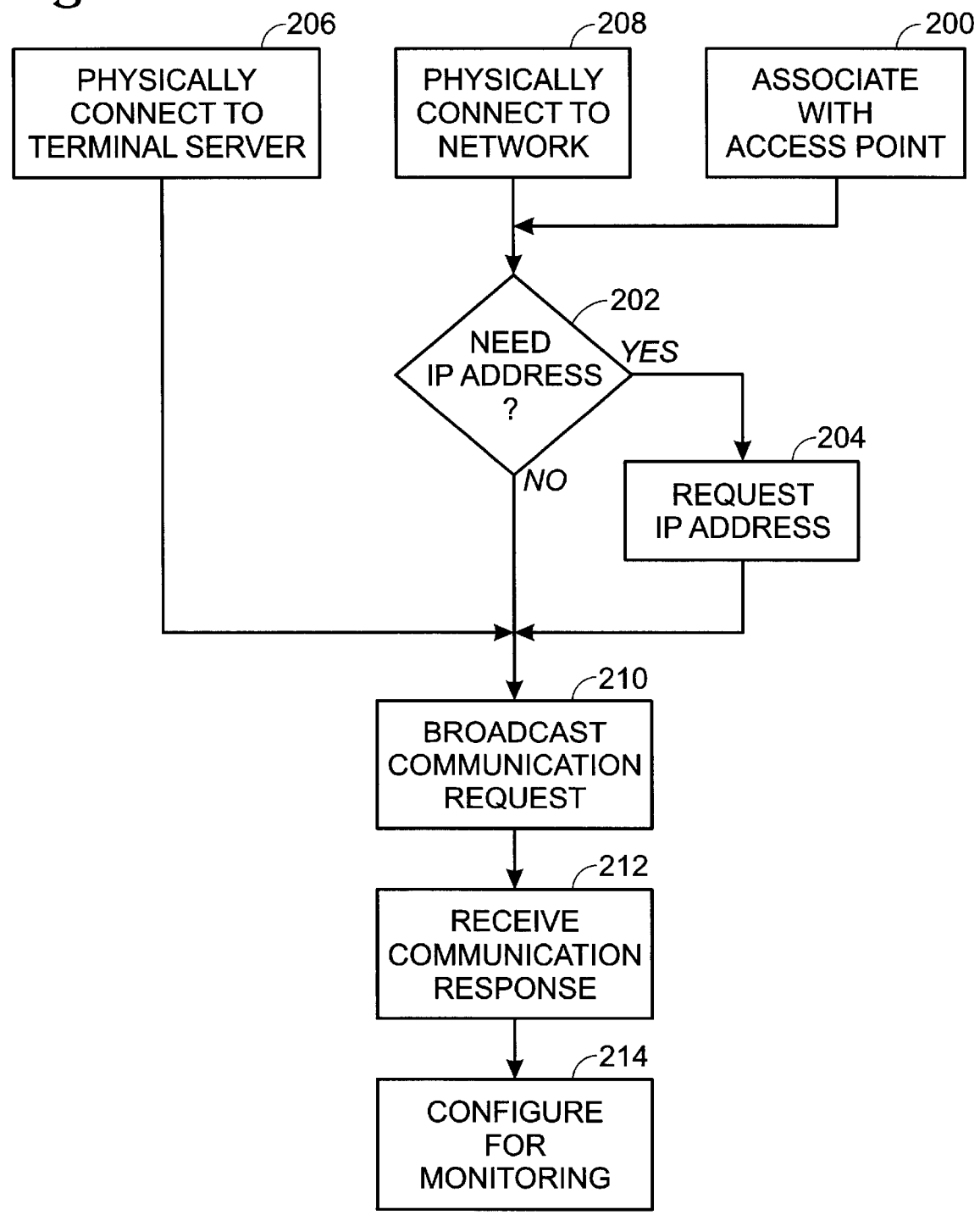
FIG. 11 is a flowchart illustrating an exemplary rendezvous process according to the present invention.

The rendezvous process of the exemplary embodiment is schematically illustrated in FIG. 11. The process begins with establishing a connection to physical data transport structure 32 by any one of several methods. Where patient monitor 22 is configured to communicate using only wireless communications, the patient monitor establishes a connection to physical data transport structure 32 by associating with an access point, as indicated at 200. It will be appreciated that the process of associating with an access point may vary with varying configurations of the access point and/or varying configurations of the patient monitor. In the exemplary embodiment, wireless transceiver 104 associates with a patient monitor according to the IEEE 802.11 standard, and the details of that standard are known to those skilled in the art. Certain features of the exemplary embodiment include that (i) the patient monitors can be used in any telemetry network described herein (such as the 802.11-standard telemetry network) without user-adjustment of the communications frequency, and (ii) the patient monitors automatically scan for access points and detect access-point configuration and synchronization information.

In addition, the wireless transceiver determines which access points are within range of the patient monitor, and the current communications load on the in-range access points. Using this information, the patient monitor selects one of the in-range access points with which to communicate, and begins the authentication process which is followed by the association process. Once the authentication and association processes are complete, the connection between the patient monitor and physical data transport structure 32 is established.

In the exemplary embodiment where communications over network 30 conform to the IP protocol, each device must have an associated IP address with which to send and receive communications. In some embodiments, patient monitor 22 may have a permanently assigned IP address stored in memory device 102. Alternatively, patient monitor 22 may not have an assigned IP address, and instead may be configured to request an IP address upon establishing a connection with physical data transport structure 32, as indicated at 202 and 204. Typically, patient monitor 22 requests an IP address by transmitting a broadcast request to server 50 using the appropriate protocol (e.g., DHCP, BOOTP, etc.). The request is answered by server 50, which responds by assigning the patient monitor an IP address from a store of available IP addresses, and then transmitting a notification of the assignment to the patient monitor. Alternatively, server 50 may store a pre-assigned IP address for each device, and respond with the corresponding pre-assigned IP address. Upon receiving the assigned IP address, the patient monitor is prepared to broadcast a request for communications to one or more central stations, as will be described in more detail below.

Where patient monitor 22 is adapted to communicate using either wireless or wire communications, the process for establishing a connection to physical data transport structure 32 will vary depending on whether a wireless or wire connection is established. In the former case, the process may occur as described above, i.e., first associating with an access point, and then requesting an IP address if necessary. Alternatively, if a wire connection is to be established, the patient monitor may be physically connected to a terminal server which is connected to the network, as indicated at 206. It will be appreciated that the connection indicated at 206 may alternatively take other forms, such as a modem connection to a modem server, etc. In any case, once the connection is established and any necessary hand-shaking between the patient monitor and the terminal server is completed, the patient monitor is prepared to broadcast a request for communications to one or more central stations. Patient monitor 22 will communicate using the IP address of the server, and therefore is not required to have its own IP address.

As a further alternative, the patient monitor may be directly connected to a hard-wired connection on physical data transport structure 32 with an Ethernet or similar connection technology, as indicated at 208. As with a patient monitor that is connected to communicate using wireless communications, a patient monitor directly connected to physical data transport structure 32 may have a permanently assigned IP address, or may request the assignment of an IP address once the physical connection is established. In any event, in the hard-wired implementation, the terminal server is then prepared to initiate a request for communications to one or more central stations.

Regardless of how a patient monitor establishes a connection with physical data transport structure 32, the patient monitor must then establish communications with a central station by broadcasting a request for communications to the central station, as indicated at 210. It will be appreciated by those of skill in the art that a patient monitor may broadcast a request for communications in any of a variety of ways. In the exemplary embodiment, the patient monitor transmits the request as a UDP broadcast to all central stations. Alternatively, other communication protocols may be used.

The UDP communications request may include a variety of parameters adapted to inform the central station about the patient monitor. For example, communications requests typically include such information as the identity, type, and/or capabilities of the patient monitor, the IP and MAC (Media Access Control) addresses of the patient monitor, the version of software installed on the patient monitor, etc. The request may also include an indicator of the type of communications desired. For example, the patient monitor may request communications to establish central monitoring of a patient, download newer versions of the patient monitoring software (discussed in more detail below), or perform network maintenance, etc. This information allows the central station to determine how to respond to the request. Unless stated otherwise, the description below will assume that the patient monitor's communications request is for the purposes of establishing centralized monitoring of a patient.

In the exemplary embodiment, the communications request is passed to, and received by, all central stations of network 30, as indicated at 212. Any routers or other network devices connected to physical data transport structure 32 are configured to pass on the request to the central stations as necessary. Alternatively, the request may be conveyed to fewer than all of the central stations, or to a single central station. Each central station is configured to respond to the communications request when received. Upon receiving the first response the patient monitor transmits an acknowledgement to the central station that sent the first response. The patient monitor is configured to reject subsequent responses by transmitting a "reject" message to any central station that sends a subsequent response. The central stations are configured to cease sending responses to the communications request after receiving a "reject" message, unless a new request for communications is received.

In some embodiments, the central stations may be configured to ensure that a preferred central station responds to the communications request. For example, the central stations may be configured to recognize a patient monitor that has communicated with network 30 in the past (e.g., based upon information transmitted in the communications request), and to allow the particular central station that was previously in communication with the patient monitor to respond first. Thus, in the exemplary embodiment the central stations are configured to determine if a communications request was sent by a patient monitor which was previously in communication with a particular central station within a predefined time period. If so, the particular central station is configured to respond to the request immediately, while the remaining central stations will wait for a relatively short period of time (e.g., 10, 15, 20, 25, or 30 seconds, etc.) before responding. This priority is based on the assumption that the patient monitor is likely still connected to the same patient as during the previous communications, and that the patient is likely to be monitored at the same central station as during the previous communications. In any event, once the patient monitor receives a first response to its communications request, the patient monitor and the central station which sent the first response (hereinafter referred to as the "provisional central station") begin communicating to configure the centralized monitoring session, as indicated at 214.

As will be described in more detail below, the particular central station which serves as the provisional central station begins the process of configuring the monitoring session. However, before the centralized monitoring begins, one of the central stations of network 30 is selected to complete the configuration process and perform the central monitoring. This selected central station is referred to herein as the "primary central station." If the provisional central station is selected to be the primary central station, then no change in communications is needed, and the provisional central station assumes the role of the primary central station. Conversely, if a different central station is selected to be the primary central station, communications with the patient monitor are transferred from the provisional central station to the selected central station, which then assumes the role of primary central station.

As is known to those of skill in the art, wireless communications which have been established between a patient monitor and a primary central station may be lost or "dropped" for any of a variety of reasons. For example, the wireless transmissions may not be received by the access point and/or the wireless transceiver of the patient monitor because the patient monitor is moved out of the defined range of network 30 (i.e., out of range of any access point). Similarly, the transmissions may have been blocked by structures between the patient monitor and the access point, such as when the patient monitor is taken into an elevator or similar enclosure. Alternatively, a portion or device of network 30 may have failed, causing the communications to be dropped. As a further alternative, the battery in the patient monitor may have been replaced or discharged, causing the patient monitor to lose communications.

The response by patient monitor 22 and central stations 24 to communications dropouts may vary depending on the length and/or cause of the dropout. In the exemplary embodiment for example, a relatively brief dropout (e.g., less than approximately 10, 20, or 30 seconds, etc.), is treated as an interruption rather than as an actual loss of communications. Lost or incomplete transmissions due to such interruptions may be resent, discarded, or ignored according to the communications protocols used by the patient monitor and central stations. Once the interruption ends, the patient monitor and primary central station resume communicating as before.

In the event of a loss of communications that extends beyond a brief interruption, exemplary patient monitor 22 is configured to detect the loss and automatically attempt to restore the communications. If the patient monitor is no longer associated with an access point, the patient monitor attempts to establish an association as described in the 802.11 standard, and continues to attempt to establish an association until association with an access point is regained. Once the patient monitor re-associates with an access point (or if the patient monitor never lost the association), the patient monitor broadcasts a request for communications to the central stations, and the rendezvous process proceeds as described above. Once the patient monitor is in communication with a provisional central station, the patient monitor and provisional central station begin the process of configuring the monitoring session, as indicated at 214.

It will be appreciated that the session configuration process may proceed in any of a variety of different ways to configure a variety of different monitoring parameters. For example, the configuration process may identify which patient is being monitored, which central station will monitor the patient, which central station will control the patient monitor, what types of vital signs data should be monitored, how the vital signs data should be analyzed, what alarm conditions should be detected, how the patient monitor should function, etc. An exemplary session configuration process is indicated generally at 216 in FIG. 12. During process 216 a primary central station is selected, the monitored patient is identified, and the patient's room or other location is specified.

Figure 12:
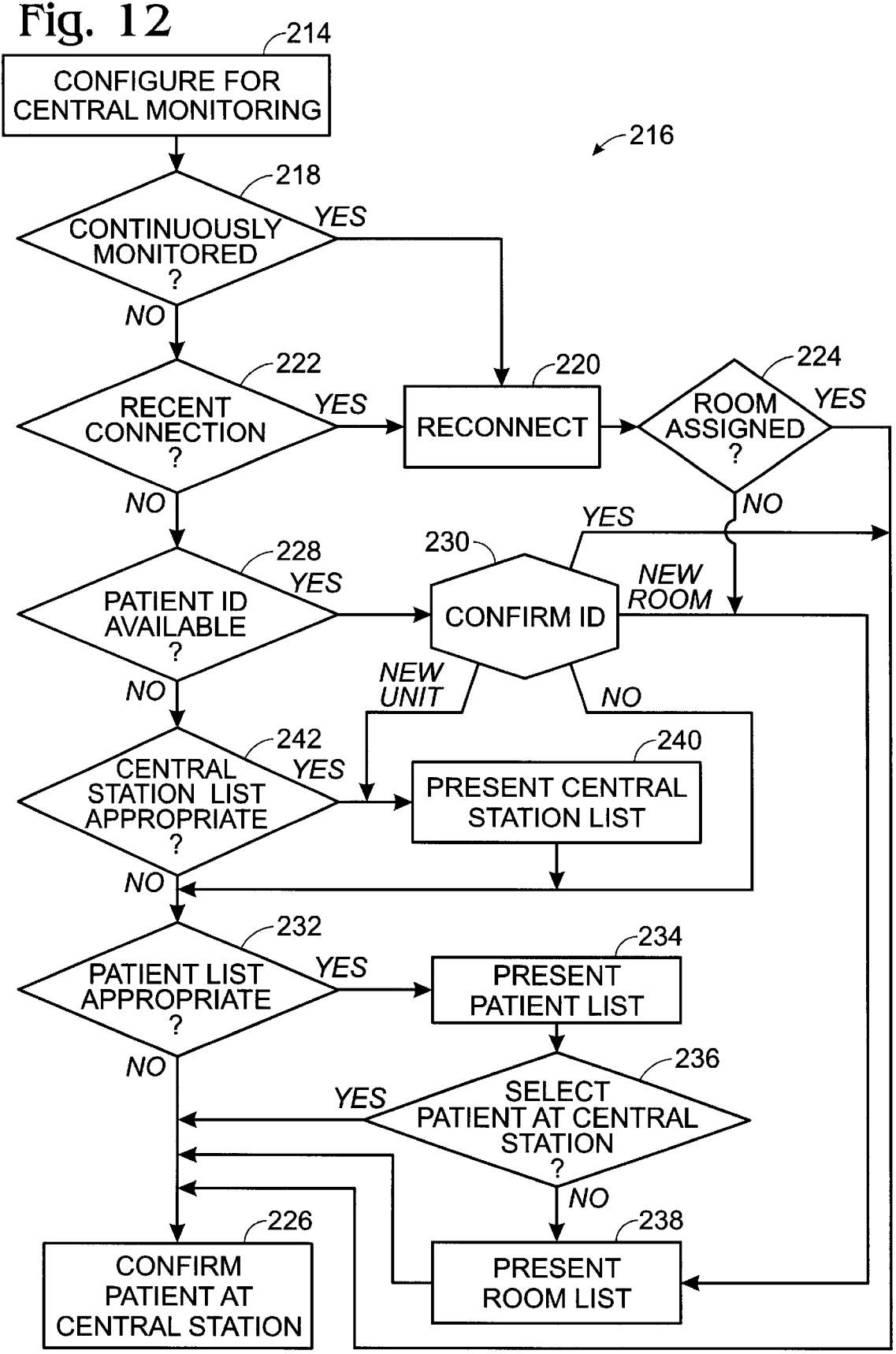
FIG. 12 is a flowchart illustrating an exemplary communications configuration process according to the present invention.

Referring to FIG. 12, the provisional central station first determines whether the patient monitor is still connected to the same patient as before the communications dropout. If such is the case, then the provisional central station assumes that the patient monitor is attempting to restore communications which were lost, and prior values for patient identity, etc., may be used. Alternatively, if the request is to establish new communications, then the central station determines the information needed to complete the configuration by querying a user of the patient monitor, as will be described in more detail below.

The provisional central station may be configured to employ a variety of different methods or mechanisms to determine whether the patient monitor is still connected to the same patient. In the exemplary embodiment for example, the provisional central station first sends a request to the patient monitor for an indication of whether the patient monitor was continuously monitoring the patient during the period the communications were lost, as indicated at 218. If the patient monitor responds affirmatively, then the patient currently being monitored is necessarily the same patient that was previously monitored.

Patient monitor 22 is configured to receive the request and detect whether it continuously monitored the same patient during the communication dropout. Typically, the patient monitor is configured to detect continuous monitoring by detecting whether the patient monitor was operational during the communications dropout, and whether vital signs data was continuously received via at least one of the sensor assemblies. For example, one exemplary ECG sensor assembly connectable to a patient is adapted to continuously send ECG vital signs data to patient monitor controller 100. If the patient monitor is disconnected from the patient during the dropout, the ECG signal will lapse. Any lapse in the ECG vital signs data is detected by the controller. Alternatively, the ECG sensor assembly, or other types of sensor assemblies, may be configured to detect actual contact with the patient. In any event, the patient monitor responds to the request by informing the provisional central station of whether the patient monitor has continuously monitored the same patient. It should be noted that the patient monitor may be monitoring the patient through sensor assemblies that do not continuously send vital signs data to the controller, and that do not detect contact with the patient. In which case, the patient monitor will be unable to confirm that it has continuously monitored the same patient, and will respond to the request from the central station accordingly.

If, at step 218, the patient monitor responds that it has continuously monitored the same patient, the provisional central station proceeds to perform a reconnect process, as indicated at 220 and as described below. Alternatively, if the patient monitor responds that it has not continuously monitored the same patient, the provisional central station then determines whether the patient monitor was recently connected to network 30, as indicated at 222. In other words, if the time period during which communications between the patient monitor and the primary central station were lost is less than a predetermined length of time, then the provisional central station concludes that the patient monitor is attempting to restore a recent connection, and proceeds to perform reconnect process 220. Otherwise, the provisional monitor concludes that the patient monitor is attempting to establish a new communications session. It should be noted that if the patient monitor was continuously monitoring the same patient during the communications dropout, then the provisional central station may safely assume the patient monitor is still connected to the same patient regardless of the length of the dropout.

The predetermined length of time that defines a recent connection may be set to any desired length of time as appropriate for a particular application. In the exemplary embodiment, the predetermined length of time is selected to be less than the minimum time period (e.g., 1, 2, 3, 4, or 5 minutes, etc.) normally needed to disconnect a patient monitor from one patient and reconnect the patient monitor to another patient. Thus, if the patient monitor was out of communication for any period of time less than that minimum disconnection/reconnection time, the provisional central station concludes that the patient monitor is still connected to the same patient. Alternatively, other time periods may be used.

The provisional central station may determine whether the patient monitor was recently connected in various ways. Typically, each central station is adapted to store patient vital signs data in database system 40. The vital signs data includes the time of collection by the patient monitor and/or receipt by the central station. Thus, the provisional central station may be configured to access database system 40 to determine the time that the last vital signs data was received from the patient monitor. Alternatively, the patient monitor may be configured to determine the length of the dropout and to inform the provisional central station, either automatically or in response to a query from the provisional central station.

In addition to the length of time during which communications were lost, the provisional central station may be configured also to evaluate other conditions at step 222. For example, if the prior communications were dropped intentionally, i.e., in response to a command by a user, the provisional central station may be configured to assume that a new patient has been connected to the patient monitor. In which case, the patient monitor is not attempting to restore a recent connection, but instead is attempting to establish a new communications connection.

As mentioned above, the provisional central station proceeds to perform a reconnect process, indicated at 220, if the provisional central station determines either that the patient monitor continuously monitored the same patient during the dropout, or that the patient monitor was recently connected to communicate with a primary central station. During reconnect process 220 the provisional central station automatically determines which patient is being monitored by the patient monitor, and which central station served as the primary central station before the communications dropout. Typically, this information is stored by the patient monitor in memory device 102, and is communicated to the provisional central station by the patient monitor. Alternatively, the information may be stored in database system 40 and read by the provisional central station via physical data transport structure 32.

In any event, if the provisional central station is not the primary central station, then the provisional central station conveys a message to the primary central station to take over the remainder of the rendezvous process. If the primary central station is available, it begins communicating with the patient monitor via physical data transport structure 32 and conducts the remainder of the configuration process as described below. Likewise, the patient monitor transmits all subsequent communications to the primary central station, and the provisional central station ends further communications with the patient monitor.

Figure 13:
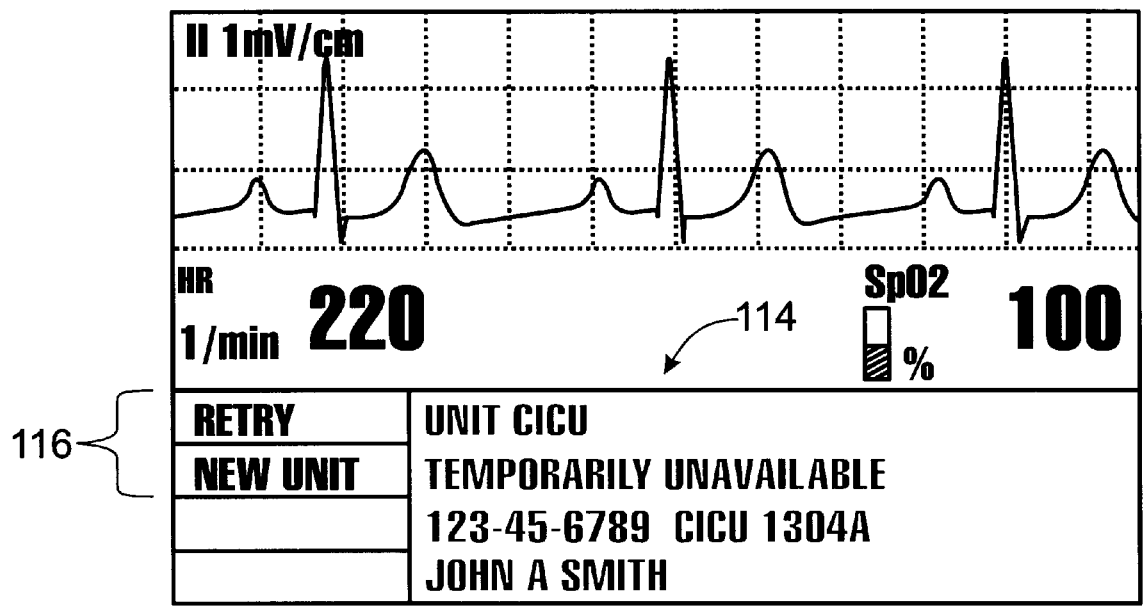
FIG. 13 is an exemplary image for display on a display screen, and including a user-interface operable to select a primary central station in accordance with the present invention.

Alternatively, if the primary central station does not respond to the provisional central station or is otherwise unavailable, the provisional central station may be configured to transmit a message to the patient monitor that the primary central station is unavailable. In the exemplary embodiment, the patient monitor controller causes display screen 84 to display a user-interface 114, such as shown in FIG. 13, including a message that the primary central station is unavailable. The user-interface may also include instruction elements 116 which are selectable by a user to instruct the central station to recheck the availability of the primary central station, or to try a new primary central station. The clinician or other user of the patient monitor may use buttons 86 to select the desired instruction, which the patient monitor then communicates to the provisional central station. Depending on the user's instructions, the provisional central station either sends another message to the primary central station to take over the communications, or transmits a list of central stations to the patient monitor. In the latter case, controller 100 causes the display device to display a list of central stations, from which the user may select using buttons 86. The patient monitor transmits the user's selection to the provisional central station, which sends a message to the selected central station to take over the communications. If the selected central station is not available, the provisional central station informs the patient monitor and the user either selects a different central station, or instructs the provisional central station to retry the selected central station. This process may be repeated until an available central station is selected to act as the primary central station. The selected central station then begins communicating with the patient monitor and conducts the remainder of the configuration process.

Once the primary central station takes over the communications with the patient monitor, the primary central station is configured to determine the patient identity (patient ID) of the particular patient being monitored by the patient monitor. The primary central station determines the patient ID by transmitting a request for the patient ID to the patient monitor. If the patient monitor cannot provide the patient ID, the primary central station then accesses database system 40 to obtain the patient ID which was stored during the patient monitor's last communication session. Once the primary central station determines the identification of the particular patient being monitored by the patient monitor, the primary central station thereafter associates all vital signs data received from the patient monitor with the particular patient. In addition, the vital signs data along with other patient information may be stored on database system 40, and then retrieved for viewing and analysis at a later time.

After the primary central station has assumed the communications with the patient monitor and determined the identity of the patient being monitored, the primary central station then determines whether the patient has been assigned to a particular location, such as a room number, bed, ward, floor, etc., as indicated at 224 in FIG. 12. This information may then be displayed on central station monitor 36 to inform the clinician of the patient's assigned location. However, in view of the portability of patient monitors 22, a particular patient may be temporarily absent from his or her assigned location even though the patient is continuously monitored at the central station. In any event, the primary central station determines whether the patient has been assigned to a particular location by sending a request for the information to the patient monitor. If the patient monitor is unable to provide an assigned location, the primary central station may be configured to search database system 40 for the information.

If the primary central station is unable to determine the assigned location, the central station is configured to query the user of the patient monitor for the patient's assigned location, as will be described in more detail below. Otherwise, the rendezvous and configuration processes are complete, and the primary central station proceeds to confirm that no other patient monitor is monitoring the same patient, as indicated at 226. In addition to checking the other patient monitors in communication with the primary central station, the primary central station also communicates with other central stations in network 30 to ensure that the same patient is not being monitored by a different central station. In the event the primary central station determines that another patient monitor is monitoring the same patient, an alarm or other indication may be displayed at the primary central station and/or the patient monitor so that a different patient ID may be selected.

As described above, the patient monitor is adapted to automatically attempt to restore communications with its primary central station in the event the communications are lost. Upon reestablishing communication, the primary central station (or a provisional central station, if different than the primary central station) is configured to automatically determine whether the patient monitor is still connected to the same patient. The central station may use a variety of mechanisms and methods to determine whether the patient monitor is still connected to the same patient, including measuring the length of time of the communications dropout, and determining whether the patient monitor disconnected from the patient data during the dropout. If the patient monitor is still connected to the same patient, the central station then associates the patient monitor with the patient so that any vital signs data received from the patient monitor is also associated with the patient. It will be appreciated that the capability to automatically identify the monitored patient at the central station after a communications dropout, enables the central station to monitor a large number of patients without constant intervention by a clinician to reconfigure a patient monitor each time a dropout occurs. Furthermore, the automatic configuration ensures that centralized monitoring of the patient resumes as soon as the patient monitor restores communication with the central station.

Turning attention back to FIG. 12, if the provisional central station determines that the patient monitor is not attempting to restore lost communications, the provisional central station proceeds to configure a new monitoring session by determining the identity of the patient being monitored, the primary central station which will monitor the patient, and the patient's assigned location. When the patient monitor establishes a new communications connection with the provisional central station, the patient monitor automatically displays a notification to a user of the patient monitor on display screen 84. As will be described below, the notification typically includes a user-interface operable by a user of the patient monitor to configure the communications session.

It will be appreciated that the provisional central station may determine the identity of the monitored patient in various ways. For example, even where the patient monitor has not recently been in communication with a central station and has not been monitoring the patient continuously since its last communication with a central station, it nevertheless may be more likely than not that the patient monitor has been reconnected to monitor the same patient. In the exemplary embodiment therefore, the provisional central station first determines whether the identity of the previous patient monitored by the patient monitor is available, as indicated at 228.

To determine whether the patient ID of the previous patient is available, the provisional central station may be configured first to query the patient monitor. Exemplary patient monitor 22 is configured to store the ID of the previous patient in memory device 102, unless the patient ID is cleared by the user. Thus, the exemplary provisional central station transmits a request to the patient monitor for the previous patient ID. If the previous patient ID is available at the patient monitor, the patient monitor communicates the previous patient ID to the provisional central station. Otherwise, the patient monitor responds that no patient ID is available.

If the patient ID is not available at the patient monitor, the provisional central station may be configured to search database system 40 for the previous patient ID associated with the patient monitor. Alternatively, if the patient monitor is connected to physical data transport structure 32 via a hard-wired connection, the provisional central station may be configured to search the database system for the previous patient ID associated with the particular location of the hard-wired connection. This strategy is based on the likelihood that the patient who was previously in the room with the hard-wired connection has not been moved since the last communications session. In the exemplary embodiment, the provisional central station is configured to search for the patient ID associated with the patient monitor if the patient monitor is communicating via wireless transmissions, and to search for the patient ID associated with the particular location of the hardwired connection if the patient monitor is communicating via wire.

Figure 14:
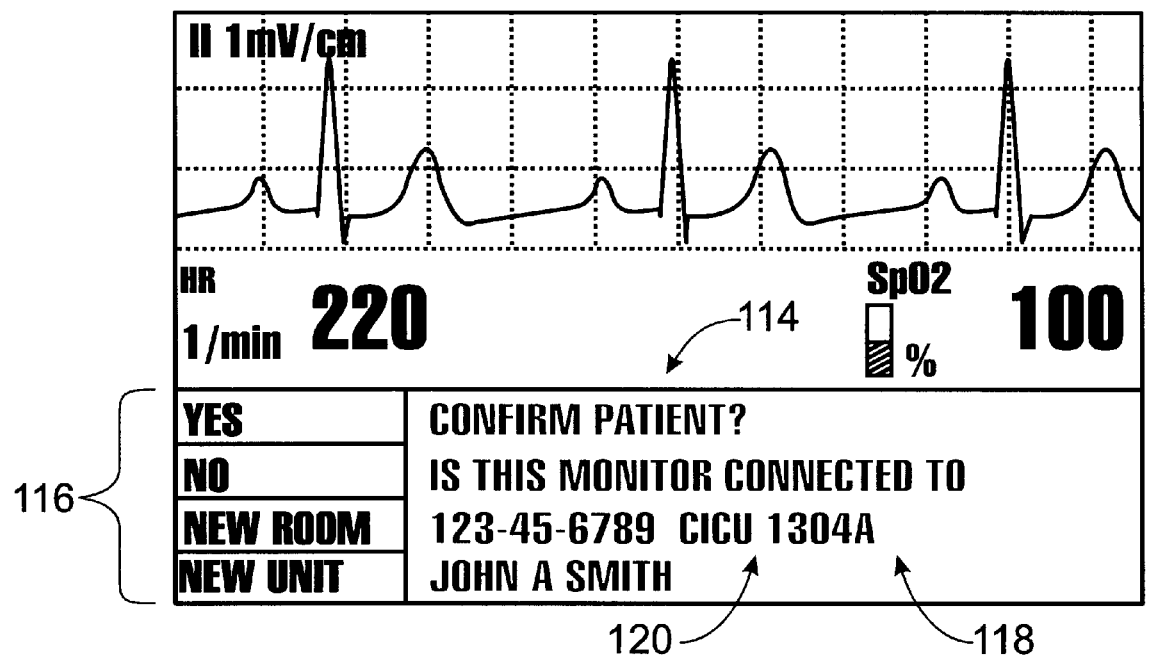
FIG. 14 is an exemplary image for display on a display screen, and including a user-interface operable to confirm a monitoring configuration in accordance with the present invention.

If the previous patient ID is available (either from the patient monitor or the database system), the provisional central station communicates an instruction to the patient monitor to confirm whether the patient currently being monitored is the same as the last patient monitored, as indicated at 230. In response, controller 100 automatically causes display screen 84 to display a user-interface 114, such as illustrated in FIG. 14. The user-interface displays the previous patient's identity (i.e., the patient's name, identifying number, and/or other identifying designation) and asks the user to confirm that the patient monitor is connected to the previous patient. Exemplary user-interface 114 also includes instruction elements 116 which are selectable by the user to indicate that the patient monitor is or is not connected to the previous patient. In the exemplary embodiment, the user-interface also displays the patient's assigned location, indicated at 118, and the central station that previously monitored the patient, indicated at 120. Thus, the clinician or other user is prompted by user-interface 114 to confirm that the same patient is being monitored, and is assigned to the same location, and is to be monitored by the same central station. Alternatively, the user may indicate that a new patient is being monitored, or that the patient has been assigned to a new location, or that the patient should be monitored by a different central station. The user's selection is communicated by the patient monitor to the provisional central station.

As shown in FIG. 12, if the user confirms the previous patient, location and primary central station (i.e., by selecting the instruction element labeled "YES"), the rendezvous and configuration processes are complete, and the primary central station proceeds to confirm that no other patient monitor is monitoring the same patient, as indicated at 226 and as discussed above. It should be noted that if the provisional central station is not the primary central station, then the provisional central station sends a request to the primary central station to take over the communications and complete the configuration process, as described above.

Alternatively, if the user responds by selecting a different one of the instruction elements, the provisional central station proceeds to determine the necessary configuration information. For example, if the user indicates that the patient currently being monitored is not the previous patient (i.e., by selecting the instruction element labeled "NO"), the provisional central station determines whether the patient monitor is configured to display a list of patients, as indicated at 232. The provisional central station may determine whether the patient monitor is configured to display a list of patients in various ways, including by sending a query to the patient monitor for its capabilities, or by accessing database system 40 to ascertain the capabilities of the patient monitor based on the type of patient monitor. As mentioned above, the type of the patient monitor may be transmitted to the provisional central station during the initial portion of the rendezvous process.

If the patient monitor is not configured to display a list of patients, then the patient ID confirmation process is passed to the central station, as indicated at 226. The central station typically is configured to display a user-interface allowing a clinician to specify the patient ID and the patient's assigned location. In addition, the clinician may instruct the central station to transfer communications with the patient monitor to a different central station, as will be described in more detail below. If, on the other hand, the patient monitor is configured to display a list of patients, the central station accesses database system 40 to identify at least some of the patients admitted to the hospital, and transmits a list of those patients to the patient monitor.

Figure 15:
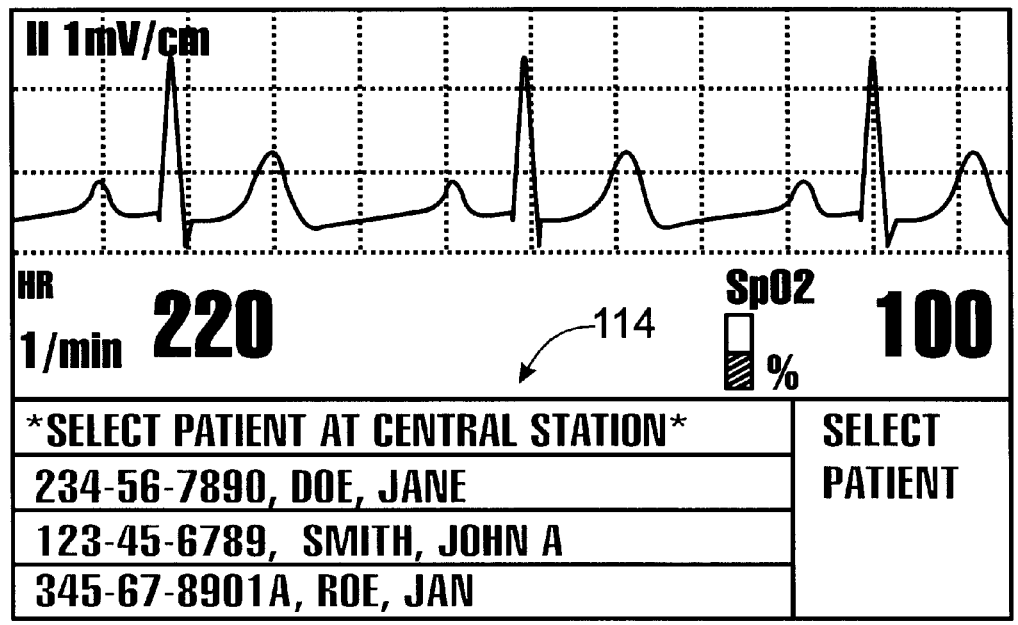
FIG. 15 is an exemplary image for display on a display screen, and including a user-interface operable to identify a patient being monitored in accordance with the present invention.

As indicated at 234, exemplary controller 100 displays the list of patients on display screen 84. An exemplary display screen presenting a list of patients is illustrated in FIG. 15. Rather than identifying the patient at the patient monitor, the clinician may operate buttons 86 to instruct that the patient's ID be selected at the central station, as indicated at 236. In which case the patient ID confirmation process is passed to the central station, as indicated at 226 and as discussed above. Alternatively, the clinician may select the ID of the monitored-patient from the patient list. The patient's ID is then communicated to the central station by the patient monitor. Next, the central station transmits a list of locations to the patient monitor controller, which displays the list to the user, as indicated at 238. Once the user selects the patient's assigned location from the list, the controller communicates the information to the central station. Finally, the central station confirms the patient is not being monitored by a different patient monitor, as indicated at 226, at which point the rendezvous and configuration processes are complete.

If, at step 230, the clinician indicates that the patient has been assigned to a different location (i.e., by selecting the instruction element labeled "NEW ROOM"), the patient monitor communicates this information to the central station, which responds by sending a list of locations to the patient monitor, as described above. The clinician then selects the patient's assigned location from the list, as indicated at 238. The location assignment is communicated to the central station, which then completes the rendezvous and configuration processes by confirming that the patient is not being monitored by a different patient monitor.

Figure 16:
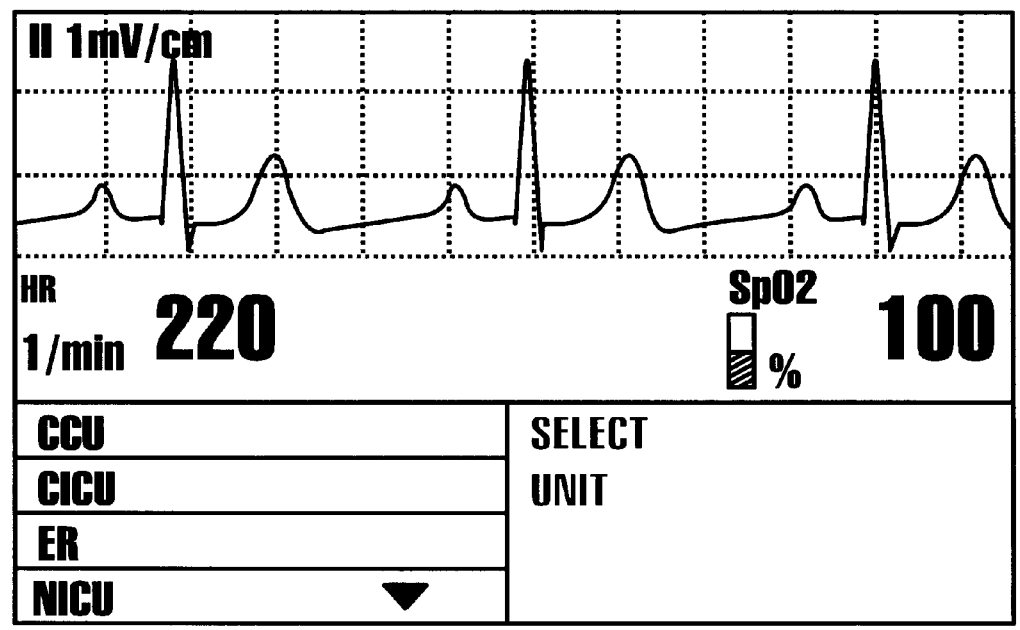
FIG. 16 is an exemplary image for display on a display screen, and including a user-interface operable to select a primary central station in accordance with the present invention.

Returning attention briefly to FIG. 14, if the central station that monitored the previous patient will not be the primary central station, the clinician requests communications with a different central station (e.g., by selecting the control element labeled "NEW UNIT"). The clinician's instruction is then communicated to the provisional central station, which responds by transmitting a list of central stations in network 30. Controller 100 displays the list of central stations on display screen 84, as indicated at 240 in FIG. 12. FIG. 16 illustrates an exemplary user-interface on display screen 84, including a list of user-selectable central stations. Once the clinician selects the desired central station from the list, the selection is communicated to the provisional central station. If the provisional central station is not the selected central station, the provisional central station sends a request to the selected central station to take over the communications and configuration process. If the selected central station is available, it takes over the communications with the patient monitor and completes the configuration process. Otherwise, the provisional central station causes the patient monitor to notify the clinician that the selected central station is unavailable, as described above.

Once the a central station is selected to be the primary central station and assumes the communications with the patient monitor, the primary central station proceeds to determine the identity of the patient and the patient's assigned location. As described above, the identity of the patient and the patient's assigned location may be entered by the clinician at the patient monitor and then communicated to the primary central station. Alternatively, the patient ID and assigned location may be specified at the primary central station. In any event, once the primary central station has confirmed the identity and the assigned location of the patient, as indicated at 226, the rendezvous and configuration processes are complete.

As described above, exemplary configuration process 216 is adapted to automatically determine the patient's identity, etc., whenever possible. This tends to minimize the amount of effort required by the clinician to configure the patient monitor for centralized monitoring. However, it will be appreciated that the provisional central station may be configured also to determine the patient identity, primary central station, and assigned location in other ways. For example, if the patient ID is not available at step 228, then the exemplary provisional central station is configured to determine whether a list of central stations should be presented to the clinician, as indicated at 232. Typically, a list of central stations is presented whenever network 30 includes more than one central station. As indicated at 240 and described above, the provisional central station transmits the list of central stations to the patient monitor for display to the clinician. The clinician selects a desired central station to serve as the primary central station. The patient monitor communicates the selection to the provisional central station, which sends a message to the selected central station to take over the communications. If the selected central station is not available, the clinician is informed to make another selection, as described above. If, at step 242, the provisional central station determines that a list of central stations should not be presented to the user, the provisional central station becomes the primary central station and completes the remainder of the configuration process.

Once the primary central station is in communication with the patient monitor, the primary central station queries the clinician for the patient ID and assigned location. Alternatively, the patient ID and assigned location may be specified at the primary central station. In any event, the primary central station then confirms that no other patient monitors are monitoring the same patient, thereby completing the rendezvous and configuration processes.

It will be appreciated by those of skill in the art that the exemplary rendezvous and configuration processes illustrated in FIGS. 11 and 12 and described above, provide a variety of capabilities for monitoring patients via medical telemetry network 30. For example, a clinician may select which central station will monitor the patient by entering instructions at the patient monitor. The clinician's instructions are communicated to the provisional central station, which then sends a request to the selected central station to take over the communications. Alternatively, the patient monitor may send a request for communications directly to the selected central station in response to the clinician's instructions. In any event, the clinician is not required to configure the patient monitor at the central station, but instead may configure and initiate the central monitoring process without leaving the patient's location.

Furthermore, exemplary patient monitor 22 is configured to automatically attempt to establish communications with a central station beginning at power-up. The patient monitor determines, without user intervention, the communications settings needed to establish a connection and to communicate with network 30 such as transmission frequency, IP addresses, synchronization, etc. Thus, a patient monitor may be shipped from its manufacturing site to any location in the world and the patient monitor will automatically configure itself to begin communications with a local medical telemetry network according to the present invention. Similarly, a patient monitor used in a network at one location may be taken to a different location, where the patient monitor will configure itself to communicate with the local medical telemetry network at the different location. As a result, patient monitors 22 may be operated without specialized training or knowledge in network communications. Instead, clinicians may place a new patient monitor in immediate use simply by powering-up the patient monitor.

If communications between a patient monitor and central station are lost, the patient monitor automatically attempts to restore the communications without requiring reconfiguration. However, if the patient monitor is attempting to establish a new communications connection, the clinician or other user of the patient monitor is automatically notified once a communications connection (either wire or wireless) is established to allow the monitoring session to be configured. A user-interface for configuring the monitoring session is automatically displayed on the patient monitor display screen. The user-interface is at least partially defined by instructions received from the central station, and is operable by a user of the patient monitor to identify the monitored patient, and to select a primary central station to perform the central monitoring, etc. After a primary central station is identified and assumes communications with, and control of, the patient monitor, the patient is continuously monitored at the primary central station. In view of the capability of the patient monitors and central stations to automatically initiate and configure the centralized monitoring process, system 20 represents a substantial advancement in patient monitoring.

It will be appreciated by those of skill in the art that the rendezvous and configuration processes described above are just one of the many ways in which the central stations and patient monitors may be configured to establish new communications and/or restore lost communications. Many variations and modifications to the rendezvous and configuration processes are possible within the scope of the invention. Therefore, it will be understood that the invention is not limited to the particular exemplary processes described above, but includes all such processes, variations, and modifications suitable for establishing communications between a patient monitor and a central monitoring station via a communications network structure.

Once patient monitor 22 has established (or restored) communications with the primary central station, the patient monitor is configured to continuously communicate the vital signs data it collects to the central station. In the exemplary embodiment, patient monitor 22 is configured to communicate all vital signs data that is collected. Alternatively, the patient monitor may be configured to communicate only a portion of the vital signs data collected. In any event, the central station is configured to receive the vital signs data and associate it with the patient being monitored. As mentioned above, the central station typically is configured to communicate simultaneously with a plurality of patient monitors, in which case the vital signs data received from each patient monitor is associated with the particular patient connected to that patient monitor.

Although patient monitor 22 is adapted to communicate with one or more central stations to establish central monitoring, the patient monitor is also configured to provide patient monitoring at the patient's location. As mentioned above, exemplary controller 100 is adapted to receive the vital signs data via sensor ports 82, and to display an image on display screen 84 that represents at least a portion of the vital signs data. It will be appreciated that the image may take any of a variety of different forms which will vary depending on the type of vital signs data collected. Thus, exemplary patient monitor 22 provides continuous local monitoring regardless of whether the patient monitor is in communication with a central station. Buttons 86 enable a clinician or other user to control a variety of functions including the information displayed on display screen 84, the format of the displayed image, the vital signs data collected, analysis of the vital signs data, alarm conditions, etc. For example, controller 100 may be controllable to display signals from selected sensor assemblies such as an ECG sensor assembly, or from a selected electrode of the ECG sensor assembly. In addition, the controller may be configured to analyze at least some of the collected vital signs data using one or more user-selectable parameters to provide additional information.

Figure 17:
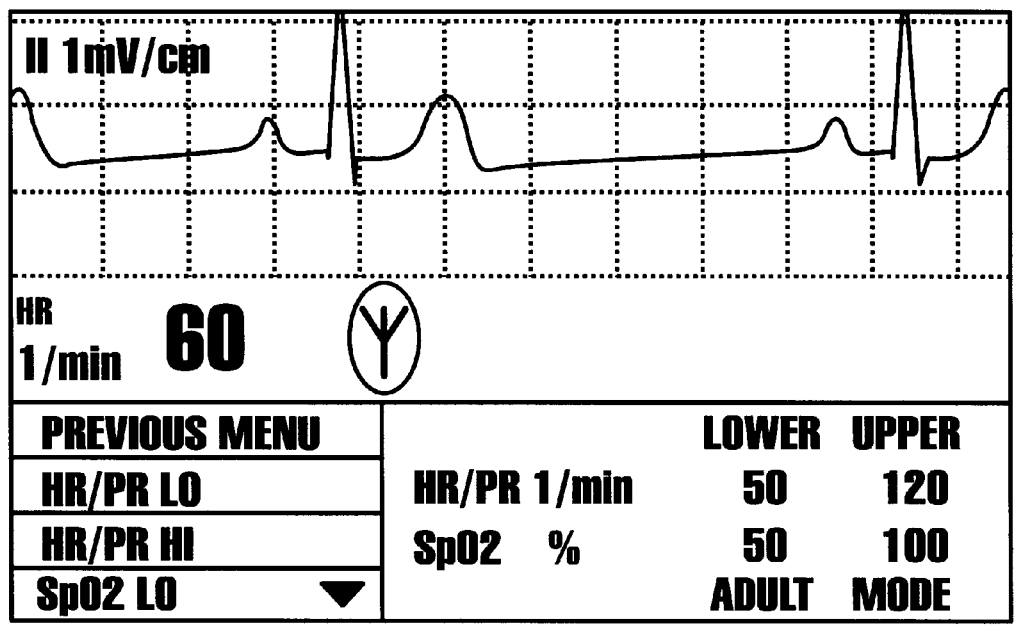
FIG. 17 is an exemplary image for display on a display screen, and including a user-interface operable to change alarm condition parameters in accordance with the present invention.

Similarly, controller 100 may be configured to analyze the vital signs data to detect whether the data is within certain defined nominal ranges, and to indicate an alarm condition if the controller detects that a portion of the data is not within the defined ranges. For example, if the upper and lower parameter values for heart rate are 120 and 50 beats per minute, respectively, the patient monitor will indicate an alarm if the detected heart rate is either greater than 120 or less than 50 beats per minute. Alternatively, any other portion of the collected vital signs data may be analyzed for alarm conditions, such as blood pressure, temperature, oxygen saturation in the patient's blood (SpO2), etc. Further, the defined nominal ranges typically are variable parameters and selectable by the user to specify particular alarm conditions for a particular patient. FIG. 17 illustrates an exemplary user-interface displayable on display screen 84, and operable by a clinician to specify the parameter values used by controller 100 to analyze the vital signs data. Alarm indications may include warning messages on display screen 84 and/or warning sounds from audio output device 92, etc.

Patient monitor 22 may also be configured to detect equipment or communications problems and provide an indication of the problem to the user. For example, controller 100 may be configured to detect a low power level in battery assembly 88, a sensor assembly that has become disconnected from the patient, a malfunction in buttons 86, lost communications, etc. The indication provided to the user may be the same as or different than the indication provided in response to the alarm conditions.

When patient monitor 22 is in communication with network 30, the primary central station may be configured to control some or all of the functions of the patient monitor. This enables a clinician to control a plurality of remotely distributed patient monitors from a single location. In addition, a central station may be configured to enable a clinician to control all patient monitors in communication with the central station to function identically. Alternatively, the clinician may control each patient monitor to function differently.

In the exemplary embodiment, the primary central station is configured and operable to change the variable parameter values which define nominal data ranges. Thus, the clinician can set or change the detection of alarm conditions at the primary central station. Instructions entered by the clinician at the primary central station are communicated to controller 100. The controller is configured to change the specified variable value in response to the instruction, and to analyze the vital signs data using the new value. Similarly, the primary central station may be configured to communicate instructions to controller 100 specifying what portions of the vital signs data should be analyzed. For example, it is known to those of skill in the art that a patient's heart rate may be determined from ECG data or from SpO2 data. Thus, where the patient monitor is collecting both ECG data and SpO2 data from a patient, a clinician at the central station may specify which type of data the controller analyzes to determine heart rate.

In addition, since the central stations typically have greater data processing capability than the patient monitors, the primary central station may be configured to analyze the vital signs data received from the patient monitor to determine additional information. For example, the primary central station may be configured to perform ST and/or arrhythmia analysis on the ECG waveform data, whereas controller 100 may analyze the ECG waveform to determine only the patient's heart rate. If the primary central station detects an alarm condition as a result of the analysis, the alarm condition may be displayed on central station monitor 36. In addition, the primary central station may communicate the alarm condition to the patient monitor and instruct controller 100 to present an indication of the alarm condition at the patient monitor. By varying where the vital signs data analysis occurs (at the central station or at the patient monitor), the patient monitor's resources may be concentrated on collecting the vital signs data and presenting information to a clinician attending the patient.

Figure 18:
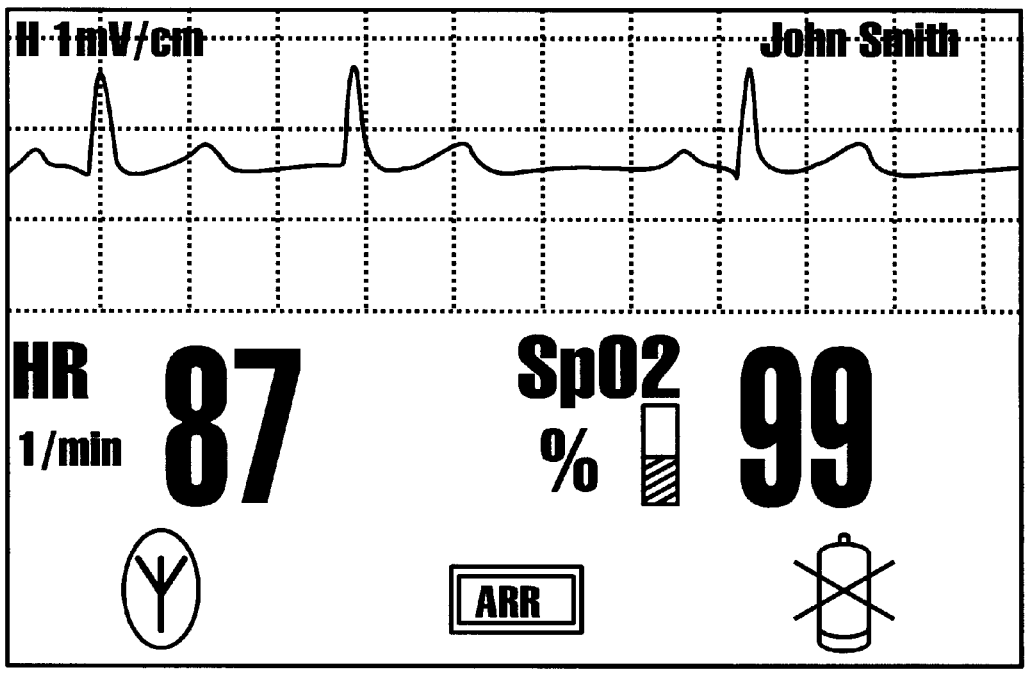
FIG. 18 is an exemplary image representing ECG data from a single electrode for display on a display screen according to the present invention.
Figure 19:
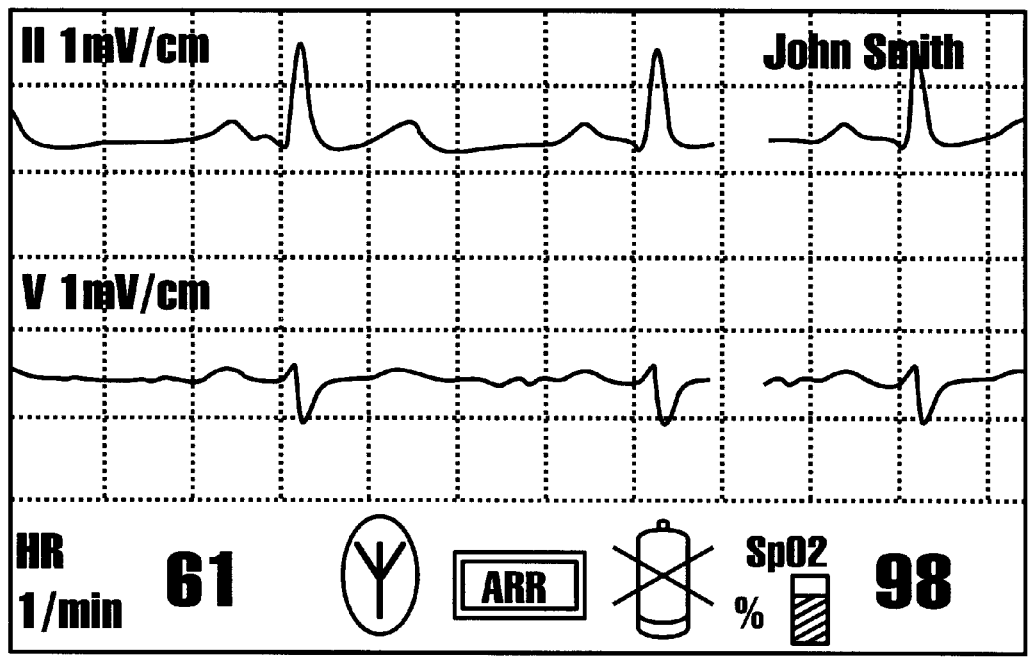
FIG. 19 is an exemplary image representing ECG data from plural electrodes for display on a display screen according to the present invention.

The primary central station may also be configured to control both the types of information and the image displayed on display screen 84. For example, where the ECG sensor assembly includes a plurality of electrodes, the clinician at the primary central station may instruct the patient monitor to display the waveform from a particular one of the electrodes, as shown in FIG. 18. Alternatively, the clinician may instruct the patient monitor to display the waveforms from a plurality of the electrodes, as shown in FIG. 19. It will be appreciated that controller 100 may be configured to control display screen 84 to display any desired information or image format in response to instructions received from the primary central station. Alternatively, the controller may be configured to turn off a portion or all of the display screen in response to instructions from the central station.

Figure 20:
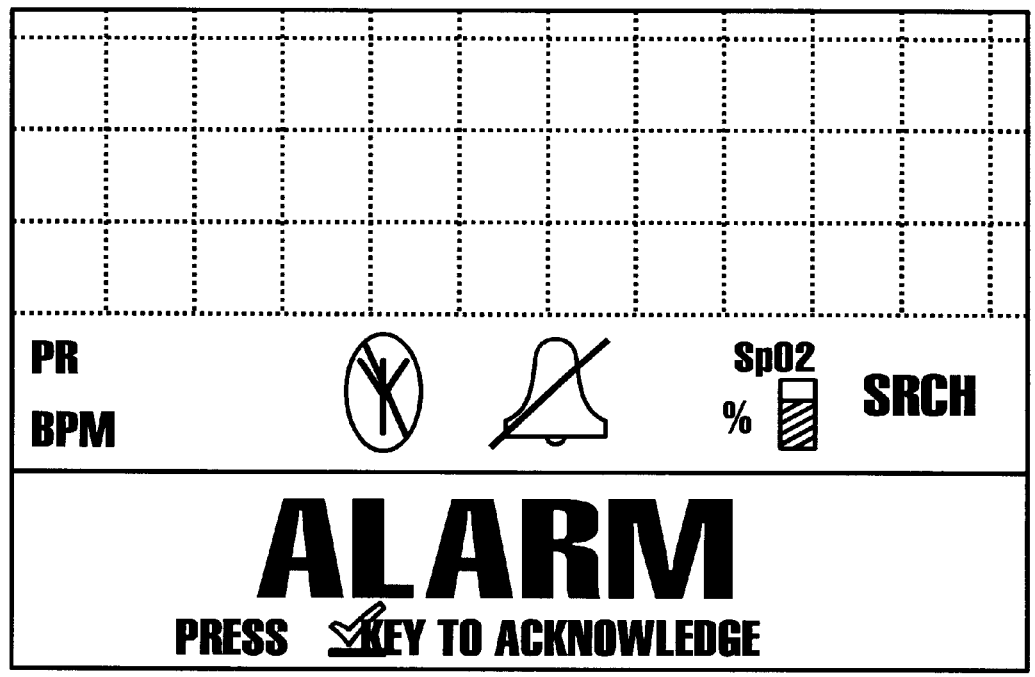
FIG. 20 is an exemplary image indicating an alarm condition for display on a display screen according to the present invention.

As described above, the patient monitor and/or the primary central station may be configured to indicate an alarm condition, equipment problem, etc., with at least one of a visible indicator or an audible indicator. For example, FIG. 20 illustrates an exemplary image displayable on display screen 84 which indicates an alarm condition. Typically, the user-interface will include an icon or other indicia to specify the cause of the alarm or problem (e.g., high heart rate, high temperature, etc.).

The patient monitor and primary central station may be configured to continue presenting the indicator for a predetermined time period, or for as long as the condition or problem persists. Alternatively, the indicator may be terminated after a specified period of time, even if the condition or problem has not ended. In the exemplary embodiment, the indicator also may be terminated (or suspended for a defined time period) if the clinician acknowledges the indication at the patient monitor and/or the primary central station. Thus, an alarm condition detected at the primary central station and communicated to the patient monitor may be acknowledged at the patient monitor. The acknowledgement is communicated to the primary central station, which then terminates the indication. As a result, a clinician attending the patient need not leave the patient's location to return to the primary central station and acknowledge the alarm.

Once communications are established between a patient monitor and a primary central station of the exemplary embodiment, the patient monitor communicates all vital signs data to the primary central station and is controlled by the primary central station. While other central stations also may receive the vital signs data and send instructions for the patient monitor (as will be described in more detail below), the primary central station maintains control of the patient monitor and is responsible for providing the central monitoring. However, control and central monitoring of the patient monitor may be transferred to a different central station, in which case the different central station is configured to take over communications with the patient monitor and assume control of the central station.

In the exemplary embodiment, a clinician may transfer control of the patient monitor to a different central station by entering a transfer instruction at the patient monitor or at the primary central station. If the clinician is at the patient monitor, controller 100 transmits the transfer instruction to the primary central station, which responds by sending a list of central stations to the patient monitor. The controller displays the list on display screen 84 to allow the clinician to select the desired central station. Once the clinician makes a selection, the patient monitor communicates the selection to the primary central station, which sends a request to the selected central station to take over the communications. If the selected central station is unavailable, the primary central station sends a notification to the patient monitor so that the clinician can make another selection. Alternatively, the patient monitor may communicate with the selected central station directly. However, if the clinician is at the primary central station when transferring control, the primary central station sends a request to the selected central station to take over the communications, as described above. Once the selected central station takes over as the new primary central station, the patient monitor communicates all subsequent vital signs data to the new primary central station.

As mentioned above, communications dropouts between the patient monitor and the primary central station may occur for a variety of reasons. Once a dropout occurs, the patient monitor begins attempting to restore the communications. However, during the dropout, the patient is not monitored at the central station. Therefore, the patient monitor may be configured to detect when central monitoring has ended, and to take additional steps to minimize any disruption due to the dropout.

In the exemplary embodiment, the patient monitor is configured to function differently when out of communication with a central station. For example, controller 100 may disable buttons 86 (e.g., by disregarding inputs at the buttons) when the controller is in communication with a central station so that the functions of the patient monitor can only be changed at the central station. Alternatively, the controller may suppress alarm indications at the patient monitor when in communication with a central station. Similarly, the controller may turn off the display when in communication with a central station to conserve battery power. The controller may be configured to perform the above steps either automatically, or in response to an instruction from the central station. However, the controller typically is configured to activate the buttons, the display and the alarm indications when not in communication with a central station.

Furthermore, some embodiments of patient monitor 22 include a button 86 operable by the patient to request clincian assistance (i.e., a "Nurse Call" button). In such case, the patient monitor may be configured to respond differently to activation of the button depending on whether the patient monitor is in communication with a central station. For example, the patient monitor may be configured to sound an audible alarm if the patient monitor is not in communication with a central station, or to forward the request for assistance to a central station without sounding an audible alarm if the patient monitor is in communication with a central station.

Similarly, when communications between the patient monitor and central station are lost, the patient monitor may be configured to automatically switch from a centrally-monitored mode, in which the vital signs data is communicated to a central station that at least partially controls the patient monitor, to a stand-alone mode, in which the vital signs data are not communicated to a central station. Typically, the patient monitor also is configured to automatically switch from the stand-alone mode to the centrally-monitored mode when the communications are restored. In other words, the patient monitor may be configured to automatically relinquish at least partial control of the patient monitoring process when in communication with a central station, but to resume full control in the event communications are lost.

In addition to automatically switching between a stand-alone mode and a centrally-monitored mode, the patient monitor may also be configured to take any one or more of a variety of steps to return to the centrally-monitored mode with minimal disruption. As described above for example, the exemplary patient monitor is configured to automatically and continuously attempt to restore the communications during the dropout. Upon restoring a connection to physical data transport structure 32, the patient monitor is configured to reestablish communications with a primary central station and, where possible, to configure the monitoring session without intervention by a clinician.

Nevertheless, the vital signs data are not communicated to the central station during the dropout. As a result, further analysis at the central station of the vital signs data received during the dropout cannot be conducted, and the vital signs data cannot be stored on database system 40 for later access. Therefore, exemplary patient monitor 22 could be configured to store at least a portion of the vital signs data collected during the dropout, and then communicate the stored vital signs data to the central station once the communications are restored. The vital signs data may be stored in memory device 102 and/or some other data storage buffer. In any event, the data collected during a dropout period would not be lost.

It will be appreciated that, depending on the length of the dropout, the vital signs data collected may exceed the patient monitor's storage capacity. Therefore, the patient monitor may be configured to store only a portion of the vital signs data collected once it detects the dropout. For example, the patient monitor may be configured to begin storing the data immediately after detecting the dropout, and then cease storing new data once the memory device is full. Alternatively, the patient monitor may be configured to begin storing the data immediately, and once the memory storage is full, to begin storing subsequent data in place of the oldest stored data. As a further alternative, the patient monitor may be configured to store only data from selected sensor assemblies rather than all sensor assemblies.

As another alternative, the patient monitor may be configured to store portions of the vital signs data which meet defined criteria. In the exemplary embodiment for example, controller 100 is configured to analyze the vital signs data received during a dropout, and to detect the occurrence of a medically-significant event based on the vital signs data. The controller only stores data that corresponds to the occurrence of a medically-significant event. Examples of typical medically-significant events include alarm conditions, arrhythmia, activation of the Nurse-Call button, etc. The amount of data stored may vary depending on the event. Typically, a continuous sequence of data is stored from a point in time several seconds or minutes before the event is detected to several seconds or minutes after the event ends. Thus, several running seconds or minutes of prior data are continuously buffered until an event is detected, at which point all or a portion of the data is stored until the event ends.

It will be appreciated that the criteria defining a medically-significant event may vary depending on the type of event, the type of sensor assembly that collects the data, the condition of the patient, the clinician's judgment, etc. The patient monitor may be pre-programmed with the criteria defining medically-significant events. Alternatively, the criteria for medically-significant events may be programmed into the patient monitor by the clinician or received from the central station. In any event, by storing only data corresponding to the occurrence of medically-significant events, the patient monitor is able to conserve data storage capacity while ensuring that communication dropouts do not prevent the primary central station from receiving the most important vital signs data.

Alternatively, or additionally, exemplary patient monitor 22 may be configured to selectively store data under other conditions. For example, controller 100 may store data at selected time intervals, or in response to an instruction from a clinician via buttons 86, etc. Thus, it will be appreciated that the patient monitor may be configured to selectively store data under any conditions as desired for a particular application.

In the embodiments described above, patient monitor 22 communicates collected vital signs data to a single central station, referred to herein as the primary central station. Likewise, the patient monitor is controlled by the primary central station. However, in other embodiments, the patient monitor may be configured to broadcast the vital signs data it collects to a plurality of central stations, and to receive and execute instructions from a plurality of central stations. As a further alternative, the primary central station may be configured to convey vital signs data received from a patient monitor to one or more other central stations.

Figure 21:
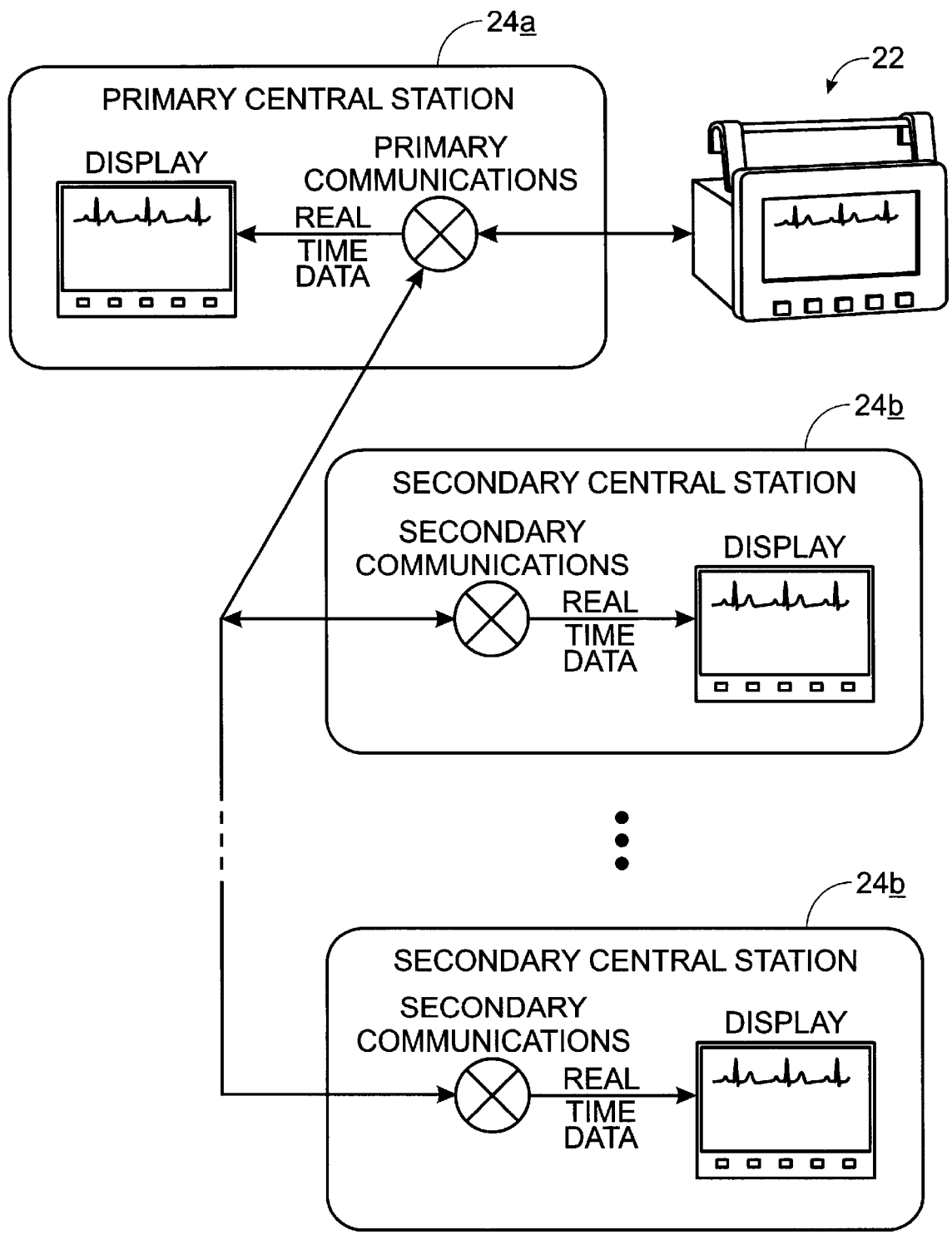
FIG. 21 is a schematic illustration of a system for monitoring a patient at plural central stations according to the present invention.

As shown in FIG. 21, exemplary primary central station 24*a* is configured to receive vital signs data from patient monitor 22, and to forward the vital signs data to one or more secondary central stations 24*b*. The vital signs data received from the patient monitor may then be displayed at the secondary central station(s) as well as at the primary central station. Typically, the secondary central station communicates a request to the primary central station to receive a particular patient's vital signs data. In response to the request, the primary central station is configured to continuously forward all vital signs data it receives that is associated with the particular patient. In addition, instructions entered at a secondary central station are communicated to the primary central station, which forwards the instructions to the patient monitor for execution. Thus, from the point of view of a clinician monitoring the patient, a secondary central station provides the same capabilities as the primary central station. However, some functions are performed only at the primary central station, such as storing or archiving the vital signs data to database system 40, performing arrhythmia analysis, etc.

It will be appreciated that communicating the vital signs data to one or more secondary central stations allows the patient's data to be monitored by clinicians at plural locations within the hospital. Thus, there is no need for a clinician to travel to a different floor, or care unit, etc., of the hospital to view the data from a particular patient. Similarly, a clinician endeavoring to monitor a particular patient is not restricted to a single location, but instead can monitor the patient from a variety of different locations.

In addition to providing central monitoring from multiple locations, secondary central stations 24b may also be configured to provide a failsafe in the event of a failure involving the primary central station. Thus, in the exemplary embodiment, at least one of the secondary central stations is configured to automatically attempt to take over communications with the patient monitor if communications between primary central station 24a and the patient monitor are lost. The secondary central station may be configured to detect the loss of communications from the primary central station in a variety of ways. In the exemplary embodiment, the secondary central station is configured to detect a loss of communications with the primary central station(even a sudden, catastrophic one such as loss of power). In response to the message, the secondary central station would then attempt to establish communications with the patient monitor. Additionally, the secondary central station is configured to monitor the communications it receives from the primary central station, and if the primary central station suddenly stops communicating (e.g., due to loss of power, malfunction, etc.) for a defined period of time, the secondary central station is configured to attempt to establish communications with the patient monitor. Alternatively, the patient monitor may be configured to transmit a request for communications to the secondary central station in the event the primary central station stops communicating.

Once the secondary central station establishes communications with the patient monitor, the secondary central station takes over the functions of the primary central station. Alternatively, the clinician may be prompted to select a new primary central station for further monitoring. Where plural secondary central stations are monitoring the patient monitor, the first secondary central station to establish communications with the patient monitor takes over as the primary central station. The new primary central station then begins forwarding the vital signs data received from the patient monitor to the remaining secondary central stations. Thus, the patient continues to be monitored at a central location staffed by clinicians, and the vital signs data collected from the patient continues to be stored for later retrieval.

As described above, patient monitor 22 and central stations 24 are configured to automatically establish and maintain communications while the patient monitor is monitoring a patient. However, patient monitor 22 may also be operable to end the communications with the central station(s). This provides an intentional and controlled termination of communications so that the patient monitor and/or the central stations do not automatically attempt to restore communications. In the exemplary embodiment, the patient monitor is operable by a clinician (e.g., using buttons 86) to transmit an end-communications signal to the primary central station. The primary central station is configured to send a confirmation of the end-communications signal to the patient monitor, which is displayed to the clinician at the patient monitor. The primary central station may also send a notification to the secondary central stations, if any.

Once the end-communications signal has been received and confirmed, the patient monitor may be powered down by the clinician without causing the primary central station to report a loss of communications. The primary central station will of course detect the loss of communication, but will be configured not to report this type of loss because it is expected. Alternatively, the primary central station will terminate the communications after a defined delay period even though vital signs data were still being received. If the patient monitor is still operating and collecting data after the communications are terminated, the patient monitor would be required to initiate the rendezvous process described above to resume centralized monitoring of the patient. Any monitoring parameters, alarm conditions, etc., that were changed at the patient monitor in response to an instruction from the central station would be reset to the nominal default values stored by the patient monitor. Likewise, any monitoring parameters, alarm conditions, etc., that were changed at the central station in response to an instruction from the clinician at the patient monitor, would be reset to the nominal default values stored by the central station.

As shown in FIGS. 1 and 2 and described above, patient monitor 22b is configured to establish communications with a central station and communicate vital signs data via either one of output port 96 or wireless transceiver 104 (illustrated in FIG. 7). In addition, exemplary patient monitor 22b is configured to detect whether output port 96 is connected to physical data transport structure 32 (either directly or through terminal server 42), and to switch automatically between wireless communications and wire communications depending on whether the output port is connected to the network structure. For example, where patient monitor 22b is initially in communications with a central station via output port 96 and the output port is disconnected from physical data transport structure 32, then controller 100 is configured to automatically associate with an access point and continue the communications with the central station via wireless transceiver 104. Similarly, where patient monitor 22b is in wireless communications with a central station when output port 96 is connected to physical data transport structure 32, controller 100 is configured to automatically cease communicating via wireless transceiver 104, and instead to communicate with the central station via the output port. Thus, the clinician can select whether patient monitor 22b communicates using wire or wireless communications by connecting and disconnecting, respectively, output port 96 to physical data transport structure 32.

As mentioned above, patient monitor 22 may also be configured to establish communications with a central station to download newer versions of the control software stored in memory device 102 and executable by controller 100. It will be appreciated that the download process may be carried out in any of a variety of different ways within the scope of the invention. It should also be understood that the control software could be for any component of the patient monitor, such as by way of examples, computer cards associated with any/all of the sensor assemblies (e.g. a pulse oximetry card, an NIBP card, etc.), computer cards associated with radio telemetry, etc.

In the exemplary embodiment, patient monitor 22 is operable by a user to request a software update. In response to the user's instructions, the patient monitor attempts to establish communications with one or more central stations, and transmits a query for new versions of the software to the central stations. The query is included as a part of the request for communications which the patient monitor broadcasts to the central stations during the rendezvous process. Each central station responding to the request indicates the version of the software stored at the central station. The patient monitor waits a defined period (e.g., 10 seconds) to receive responses from the central stations, and then selects a central station with the newest version of the software. Thus, even where the central stations have multiple versions of the software, the patient monitor is configured to determine which central station(s) has the newest version and to download the software from the central station with the newest version. This allows a system administrator to store new versions of the software on just one or a few of the central stations, and then operate the patient monitors to automatically find and download the newest software.

Once a central station with the newest version of the software is selected, the patient monitor transmits a request to the selected central station to download the new software. The selected central station responds by transmitting the new software via either wire or wireless communications, depending on whether the patient monitor is communicating via output port 96 or wireless transceiver 104. The software download may be carried out using any of a variety of methods or protocols, such as Trivial File Transfer Protocol (TFTP), etc. Typically, the patient monitor and selected central station verify that the software was accurately received at the patient monitor using one or more of a variety of error-checking methods known to those of skill in the art. Once the patient monitor receives the new software, controller 100 updates the control software by installing the new software. The controller may carry out this updating process for control software of any of components of the patient monitor as described above.

As described above, the invention provides a system for continuously monitoring a plurality of patients at one or more central stations using a plurality of portable patient monitors. The invention also provides a method for monitoring a patient at a central location, as indicated generally at 300 in FIG. 22. The method is implemented by software running on patient monitors 22, central stations 24, and/or other components of system 20. The method includes, at step 310 establishing wireless communications between a patient monitor and a communications network having at least one wireless transceiver and a plurality of central stations. Then communicating a list of the plural central stations to the patient monitor via the wireless transceiver, as indicated at step 320. Alternatively, the list of the plural central stations may be provided to, or stored on, the patient monitor in other ways. In any event, method 300 proceeds with selecting, at the patient monitor, one of the plural central stations, as indicated at 330. Then collecting, at the patient monitor, vital signs data from a patient, as indicated at step 340. The vital signs data are communicated to the wireless transceiver, at step 350, and then communicated from the wireless transceiver to the selected central station, at step 360.

A further method for monitoring patients according to the present invention is indicated generally at 400 in FIG. 23. Method 400 includes, at step 410, establishing communications between a wireless patient monitor and a central station adapted to receive vital signs data from a plurality of patients. Configuring the patient monitor to collect vital signs data from a particular one of the plural patients, at step 420. Communicating a list of the plural patients from the central station to the patient monitor, as indicated at step 430. Alternatively, the list of patients may be provided to, or stored on, the patient monitor in other ways. In any event, method 400 continues at step 440 with identifying, at the patient monitor, the particular patient. Communicating the identity of the particular patient to the central station, at step 450. Communicating the vital signs data collected from the particular patient to the central station, as indicated at step 460. Finally, associating, at the central station, the vital signs data with the particular patient, as indicated at step 470.

Figure 24:
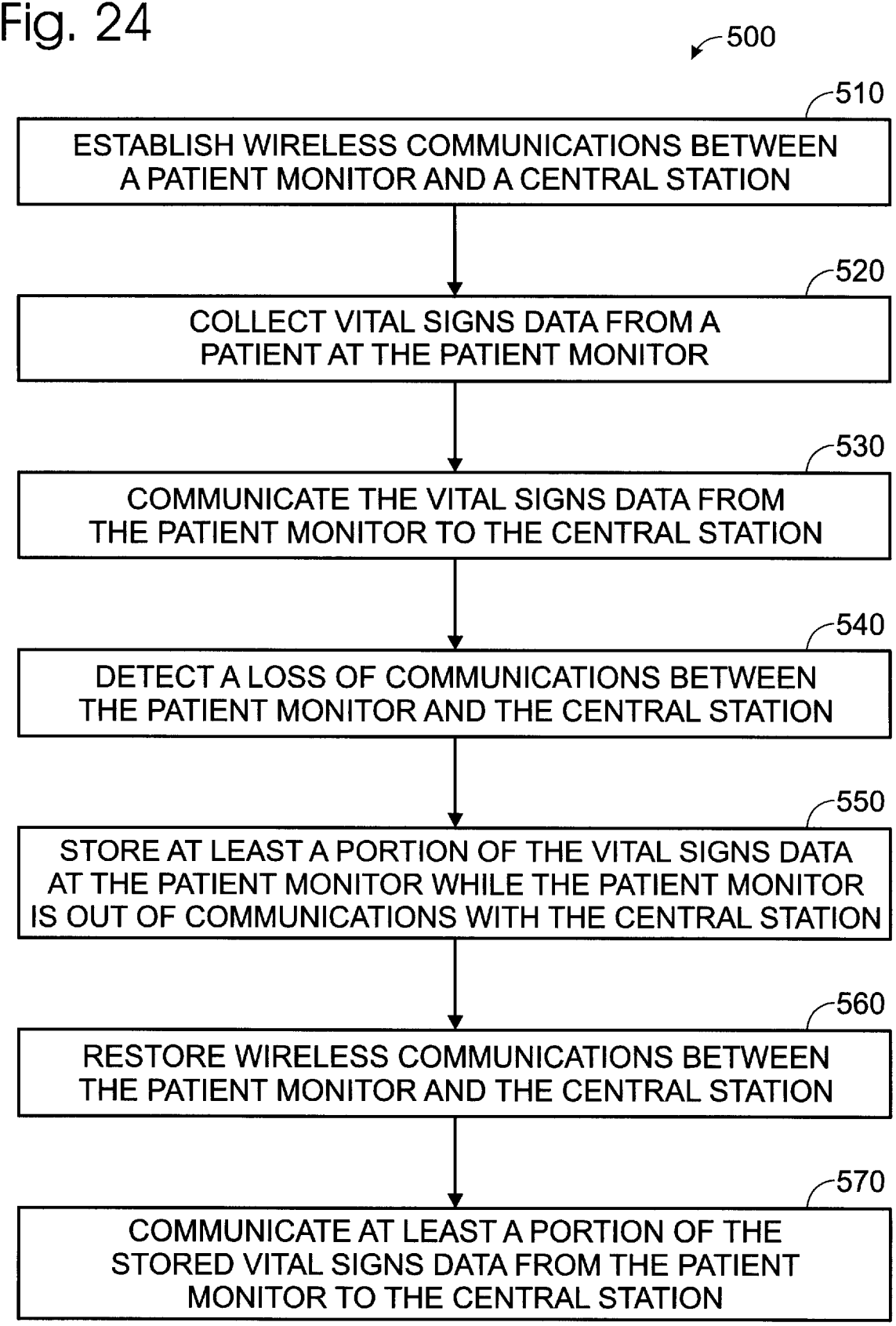
FIG. 24 is a flowchart diagram of another exemplary method for monitoring a patient at a central location in accordance with the present invention.

Another method for monitoring patients according to the present invention is indicated generally at 500 in FIG. 24. Method 500 includes, at step 510, establishing wireless communications between a patient monitor and a central station. Collecting vital signs data from a patient at the patient monitor, at step 520. Communicating the vital signs data from the patient monitor to the central station, at step 530. In the event that communications between the patient monitor and the central station are lost, detecting that loss of communications, at step 540. Storing at least a portion of the vital signs data at the patient monitor while the patient monitor is out of communications with the central station, as indicated at step 550. Restoring wireless communications between the patient monitor and the central station, at step 560. Then, communicating at least a portion of the stored vital signs data from the patient monitor to the central station, as indicated at step 570.

Another method for monitoring patients according to the present invention is indicated generally at 600 in FIG. 25, and includes establishing wireless communications between a patient monitor and a first central station, as indicated at step 610. Collecting vital signs data from a patient at the patient monitor, at step 620. Communicating the vital signs data from the patient monitor to the first central station, at step 630. So long as communications between the patient monitor and the first central station are maintained, the patient monitor continues to communicate the vital signs data to the first central station, as indicated at 640. However, in the event communications between the patient monitor and the first central station are lost, then wireless communications are automatically established between the patient monitor and a second central station, as indicated at step 650. Finally, communicating the vital signs data from the patient monitor to the second central station, at step 660. It should also be noted that when a clinician using the patient monitor transfers communication to a different central station, there is a transition time (presently that duration is in the range of about 5–10 seconds). During that transition time, the patient monitor could be configured to store data for later uploading to the different central station chosen by the clinician.

Another method for monitoring patients according to the present invention is indicated generally at 700 in FIG. 26. Method 700 includes, at step 710, establishing wireless communications between a patient monitor connected to a particular one of plural patients and a central station. Communicating the identity of the particular patient from the patient monitor to the central station, at step 720. Collecting vital signs data from the particular patient at the patient monitor, as indicated at 730. Then, communicating the vital signs data to the central station, at step 740, and associating, at the central station, the patient monitor with the particular patient, as indicated at step 750. So long as communications between the patient monitor and the central station are maintained, the patient monitor continues to communicate the vital signs data to the central station, which associates the vital signs data with the particular patient, as indicated at 760. In the event communications between the patient monitor and the central station are lost for a period of time, reestablishing the communications between the patient monitor and the central station, at step 770. Then, automatically determining, at the central station, whether the patient monitor is still connected to the particular patient, as indicated at step 780. Finally, if the patient monitor is still connected to the particular patient, then associating the patient monitor with the particular patient.

In addition to the exemplary methods for monitoring patients described above, it will be appreciated that the configuration and operation of system 20 is not limited to the exemplary methods as many variations and modifications are possible within the scope of the invention. Further, system 20 may be configured and operated to monitor patients according to a variety of other methods within the scope of the invention. Therefore, it will be understood that all such methods, variations and modifications are within the scope of the invention.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

What is claimed is:

1. A wireless medical telemetry system, comprising:
   at least one wireless patient monitor configured to monitor a patient by continuously collecting vital signs data from the patient;
   a first central station associated with one or more wireless transceivers, and adapted to establish communications with the at least one patient monitor and continuously receive the vital signs data therefrom via the one or more wireless transceivers; and
   a second central station associated with the one or more wireless transceivers, and adapted to continuously receive the vital signs data via the one or more wireless transceivers;
   where the second central station is configured to automatically attempt to establish communications with the at least one patient monitor and continuously receive the vital signs data in place of the first central station in the event the communications between the first central station and the at least one patient monitor are lost.

2. The system of claim 1, where the second central station is configured to monitor the communications between the first central station and the at least one patient monitor.

3. The system of claim 2, where the second central station is configured to monitor the communications between the first central station and the at least one patient monitor by receiving the vital signs data from the first central station, and to automatically attempt to establish communications with the at least one patient monitor if the second central station stops receiving the vital signs data from the first central station.

4. The system of claim 1, where the at least one patient monitor is configured to transmit a request to establish communications to the second central station via the one or more wireless transceivers in the event the communications with the first central station are lost.

5. The system of claim 1, further comprising a third central station associated with the one or more wireless transceivers, and adapted to receive vital signs data via the one or more wireless transceivers, and where both the second and third central stations are configured to automatically attempt to establish communications with the at least one patient monitor and receive the vital signs data in place of the first central station in the event the communications between the first central station and the at least one patient monitor are lost.

6. The system of claim 1, where the first central station is configured to communicate instructions to the at least one patient monitor to control the patient monitor, and where the second central station is configured to automatically attempt to assume control of the at least one patient monitor in the event the communications between the first central station and the at least one patient monitor are lost.

7. A method for monitoring a patient, comprising:
   establishing wireless communications between a patient monitor and a first central station;
   continuously collecting vital signs data from a patient at the patient monitor;
   continuously communicating the vital signs data from a patient at the patient monitor;
   continuously communicating the vital signs data from the patient monitor to the first central station; and
   if communications between the patient monitor and the first central station are lost, automatically establishing wireless communications between the patient monitor and a second central station, and continuously communicating the vital signs data from the patient monitor to the second central station.

8. The method of claim 7, further comprising monitoring, at the second central station, the communications between the patient monitor and the first central station.

9. The method of claim 8, where the step of monitoring includes receiving, at the second central station, the vital signs data from the first central station.

10. The method of claim 7, where the step of establishing wireless communications between the patient monitor and the second central station includes detecting, at the patient monitor, a loss of communications with the first central station, and transmitting a request to establish communications from the patient monitor to the second central station.

* * * * *